United States Patent
Matsuoka et al.

(10) Patent No.: US 8,333,875 B2
(45) Date of Patent: Dec. 18, 2012

(54) SENSOR CONTROL DEVICE

(75) Inventors: Mikiyasu Matsuoka, Kariya (JP);
Tomoo Kawase, Aichi-ken (JP); Eiichi Kurokawa, Okazaki (JP)

(73) Assignee: Denso Corporation, Kariya (JP)

( * ) Notice: Subject to any disclaimer, the term of this patent is extended or adjusted under 35 U.S.C. 154(b) by 905 days.

(21) Appl. No.: 12/010,682

(22) Filed: Jan. 29, 2008

(65) Prior Publication Data

US 2008/0185289 A1   Aug. 7, 2008

(30) Foreign Application Priority Data

Feb. 5, 2007   (JP) ................................. 2007-025070
Jul. 11, 2007   (JP) ................................. 2007-182587

(51) Int. Cl.
*G01N 27/41* (2006.01)
(52) U.S. Cl. ...................................... 204/425; 204/406
(58) Field of Classification Search .......... 204/400–435; 205/775–794.5; 123/672–703; 73/23.31, 73/23.32
See application file for complete search history.

(56) References Cited

U.S. PATENT DOCUMENTS

| | | | | |
|---|---|---|---|---|
| 4,265,714 A | * | 5/1981 | Nolan et al. | 205/779.5 |
| 5,298,865 A | * | 3/1994 | Denz et al. | 324/509 |
| 5,668,312 A | * | 9/1997 | Kaman | 73/114.61 |
| 5,721,513 A | * | 2/1998 | Yuasa | 330/282 |
| 5,753,815 A | * | 5/1998 | Murata | 73/204.15 |
| 5,810,997 A | * | 9/1998 | Okazaki et al. | 205/784.5 |
| 5,980,710 A | * | 11/1999 | Kurokawa et al. | 204/425 |
| 6,148,808 A | * | 11/2000 | Kainz | 123/673 |
| 7,481,913 B2 | * | 1/2009 | Kawase et al. | 204/406 |
| 2004/0089545 A1 | | 5/2004 | Kawase et al. | |
| 2007/0284248 A1 | | 12/2007 | Kawase et al. | |

FOREIGN PATENT DOCUMENTS

| | | |
|---|---|---|
| JP | 9-061397 | 3/1997 |
| JP | 2004-205488 | 7/2004 |
| JP | 2006-275628 | 10/2006 |
| JP | 2007-315943 | 12/2007 |

\* cited by examiner

*Primary Examiner* — Kaj K Olsen
*Assistant Examiner* — Susan D Leong
(74) *Attorney, Agent, or Firm* — Nixon & Vanderhye P.C.

(57) ABSTRACT

A current detection resistance in a sensor control device is connected to a sensor element. The current flowing in the sensor element is detected through the current detection resistance. The current detection resistance is connected to an inverting amplification circuit for outputting an air/fuel output voltage to be transferred to a microcomputer. An offset setting circuit is connected to one input terminal of an operational amplifier in the inverting amplification circuit. The offset setting circuit is comprised of a switching element, a resistance connected in series to the switching element, and two dividing voltage resistances whose common node is connected to the resistance. The offset setting circuit generates and gives an offset to the A/F output voltage. The switching element is turned ON and OFF based on an offset switching signal transferred from the microcomputer.

11 Claims, 14 Drawing Sheets

SENSOR CONTROL DEVICE

CROSS-REFERENCE TO RELATED APPLICATION

This application is related to and claims priority from Japanese Patent Applications No. 2007-25070 filed on Feb. 5, 2007 and No. 2007-182587 filed on Jul. 11, 2007, the contents of which are hereby incorporated by reference.

BACKGROUND OF THE INVENTION

1. Field of the Invention

The present invention relates to a sensor control device for controlling the operation of a sensor element made of solid polymer electrolyte (SPE) capable of measuring a gas concentration of a specific component contained in a target gas in a wide range.

2. Description of the Related Art

Such a type of a sensor control device for controlling the operation of a sensor element made of solid polymer electrolyte (SPE) is concretely realized or used as an A/F ratio (A/F ratio) detection device capable of detecting an oxygen concentration in the exhaust gas of (or combustion gas) emitted from an internal combustion engine mounted on a motor vehicle, for example. Such an A/F ratio is the mass ratio of air to fuel present during combustion. The sensor control device transfers a detection result to an A/F ratio control system composed of an engine ECU (electric control unit). The ECU performs a stoichiometry combustion control of carrying out the feedback of the A/F ratio around a stoichiometry value (as a theoretical A/F ratio) or performs a lean combustion control of carrying out the feedback of the A/F ratio in a predetermined lean area.

More recently, there are demands such as automobile emission control and on-board diagnostics (or OBD), for example. The automobile emission control covers all the technologies that are employed to reduce the air pollution-causing emissions produced by automobiles. The OBD is a computer-based system built into vehicles and trucks. An OBD system is designed to monitor the performance of some of an engine's major components for controlling emissions. Those recent demands need to increase the performance of controlling the stoichiometry combustion and also to expand the A/F ratio detecting range toward the atmosphere condition in addition to the lean area. For example, there is a necessity to detect deterioration of sensors, such as a clogged state when a fuel supply is halted in usual operation, as OBD. It further becomes important to enhance the fuel consumption as well as improvement of exhaust gas emission control. It is therefore very important to perform the feedback control of a fuel rich condition in a high load operation of an engine.

The inventors according to the present invention have proposed improved techniques. For example, Japanese patent laid open publication No. JP 2004-205488 has disclosed a sensor control device equipped with a plurality of amplifiers having different amplification factors. In the sensor control device, A/F ratio detection signals are generated according to the outputs from the plural amplifiers. The above technique intends to detect the A/F ratio in a wide A/F ratio detection range and to increase the detection accuracy for the A/F ratio in a desired air/fuel detection range. The related art technique described above can detect an A/F ratio with high accuracy in the desired air/fuel detection range.

However, the related art techniques contain disadvantage, namely, need to incorporate the plurality of amplification circuits (composed of operational amplifiers) and therefore need to have a large circuit size and plural terminals through which signals are input and output. Thus, the related art techniques are still necessary to improve and eliminate the above disadvantage.

There is another related-art technique capable of setting a stoichiometry narrow range near a stoichiometry value and a lean narrow range in a fuel lean area in addition to switching the wide range and a narrow range as the A/F ratio detection range. For example, Japanese patent laid open publication No. JP 2006-275628 has disclosed a sensor control device, in which a differential amplification circuit inputs an element current signal flowing through a sensor element and then amplifies the input one by a specific amplification factor. In the sensor control device disclosed in JP 2006-275628, an offset voltage is supplied to one input terminal of the differential amplifier and the stoichiometry narrow range near a stoichiometry value and the lean narrow area in a lean value as the A/F ratio detection range by switching the offset-voltage.

FIG. 14 is a diagram showing a part of a configuration of a related-art sensor control circuit disclosed in JP 2006-275628 described above. FIG. 14 shows a circuit diagram which corresponds to FIG. 2 disclosed in JP 2006-275628. In particular, FIG. 14 omits a configuration capable of changing the signal amplification factor for brevity.

In FIG. 14, reference number 101 designates a shunt resistance as a current detection resistance through which a current flowing through an element is detected. Both ends of the shunt resistance 101 are connected to buffers 102 and 103, respectively. One terminal of a resistance 112 is connected to the buffer 102. The other terminal of the resistance 112 is connected to an inverting input terminal (as a negative (−) input terminal) of an operational amplifier 111 which forms a differential amplification circuit 110. A resistance 113 is connected between the negative (−) input terminal and an output terminal of the differential amplifier 111. One terminal of the resistance 114 is connected to the buffer 103. The other terminal of the resistance 114 is connected to a non-inverting input terminal (as a positive (+) terminal) of the operational amplifier 111. A switch 116 is connected to the positive (+) input terminal of the operational amplifier 111 through a resistance 115. The switch 116 selecting one of the contacts connected to a node of a voltage V11 determined by voltage dividing resistances 116 and 117 and to a node of a voltage V12 (not equal to the voltage V11) determined by voltage dividing resistances 119 and 120. The voltage potential of the power source is divided by the four resistances 117 to 120.

In the sensor control circuit having the above configuration shown in FIG. 14, the switch 116 can switch the offset voltage for the differential amplification circuit 110 to the stoichiometry narrow range near the stoichiometry value and the lean narrow area in the lean area.

However, in the sensor control device disclosed in JP 2006-275628, the resistance value at the non-inverting input terminal (as the positive (+) input terminal) of the operational amplifier 111 is changed by the switching operation of the switch 116, and this results in the fluctuation of the amplification factor and the like of the operational amplifier 111. That is, when it is considered that the values of the resistances 112 and 113 connected to the inverting input terminal (as the negative (−) terminal) of the operational amplifier 111 are designated by R11 and R12, and the values of the resistances 114 and 115 connected to the non-inverting input terminal (as the positive (+) terminal) of the operational amplifier 111 are designated by R13 and R14, the resistance value determined by the dividing voltage resistances 117 and 118 are designated by R15, and the resistance value determined by the dividing voltage resistances 119 and 120 is designated by R16. In this case, the differential amplification circuit 110 can perform a signal amplification in a desired amplification factor (=R12/R11) unless the following condition is satisfied:
(1) R11=R13; and
(2) R12=R14+R15, or (3) R12=R14+R16.

However, when R15 is not equal to R16 (R15≠R16), one of (2) and (3) cannot be satisfied. This phenomenon has a drawback to vary the signal amplification factor and gas concentration detection range by the operation of the switch 16, contrary to the expectation.

SUMMARY OF THE INVENTION

It is an object of the present invention to provide a sensor control device capable of setting and selecting one of a plurality of different gas concentration detection ranges, and detecting a gas concentration of a target detection gas with high accuracy under each gas concentration detection range selected.

To achieve the above purposes, the present invention provides a sensor control device for controlling an operation of a sensor element made up of solid polymer electrolyte capable of detecting a concentration of a specific gas component contained in a target gas in a wide detection range. The sensor control device has a current detection resistance, an amplification circuit, an offset setting circuit, and an offset switching means. Through the current detection resistance, a current flowing in the sensor element is detected and an element current signal is generated. The amplification circuit inputs the element current signal through one of positive and negative input terminals thereof, and amplifies the element current signal. The offset setting circuit sets an offset (or an offset value). The offset setting circuit is connected to a middle node between an input resistance and one or more feedback resistances in a feedback line (or a feedback wiring) for the amplification circuit. The offset switching means switches the offset determined by the offset setting circuit according to the element current signal, which is continuously supplied from the sensor element, regarding the concentration of the specific gas component in the target gas.

As the main point of the present invention, the sensor control device has the amplification circuit capable of amplifying the element current signal received through at least one of positive and negative input signal terminals thereof. The sensor control device can set or add an offset (or an offset value) to an output signal output from the amplification circuit because the offset setting circuit is connected to a middle node between the input resistance and the feedback resistances in the feedback line for the amplification circuit. That is, the amplification circuit and the offset setting circuit form an adder circuit. The output signal from the amplification circuit to a microcomputer (designated by reference number 10 in FIG. 1) is the signal obtained by adding the element current signal corresponding to the current flowing through the sensor element and the offset. The configuration having the single amplification circuit (not having a plurality of amplification circuits in the related art techniques), can select and set the optimum gas concentration detection range. In this configuration, because the current value (as the offset) supplied from the offset setting circuit and to be added to the output current from the amplification circuit is known in advance, it is possible to accurately detect the gas concentration of the target gas.

Returning to the related art techniques, the conventional sensor control device having the differential amplification circuit shown in FIG. 14 has a possibility of fluctuating the signal amplification factor and the gas concentration detection range, contrary to the expectation. Such a fluctuation occurs in the differential amplification circuit (see FIG. 14) by the state in which the feedback resistance value becomes different from the ground resistance value by switching the offset voltage (R12=R14+R15 or R12=R14+R16 is not satisfied, in FIG. 14.)

On the contrary, according to the sensor control device of the present invention, because the offset setting circuit is connected to the middle node between the input resistance and one or more feedback resistances in the feedback line for the amplification circuit, it is possible to avoid the occurrence of any fluctuation of the feedback resistance value and the ground voltage value by switching the offset (corresponding to an offset voltage).

According to the present invention described above in detail, it is possible to set one of the different gas concentration detection ranges and to perform the optimum gas concentration detection in each detection range. Further, it is preferable that the amplification circuit is an inverting type or a non-inverting type amplification circuit (see FIG. 1, FIG. 9, and FIG. 13) for inputting the element current signal detected by the current detection resistance through one of the positive and negative input signal terminals thereof, and to amplify the element current signal. Still further, it is preferable that the amplification circuit is a differential amplification circuit (see FIG. 12) to input the voltage signals at both the ends of the current detection resistance through the positive and negative input signal terminals thereof, and to amplify a difference of the voltage signals.

In both the cases of the amplification circuits in the sensor control device according to the present invention, it is possible to realize or maintain the condition where the feedback resistance value becomes equal to the ground resistance value in the amplification circuit before and after the offset-setting switching operation by the offset switching means.

In the sensor control device as another aspect of the present invention, the offset switching means switches the offset (or offset value) determined by and transferred from the offset setting circuit by connecting/disconnecting the middle node between the input resistance and the feedback resistance in the feedback line of the amplification circuit to/from the offset setting circuit. In the sensor control device as another aspect of the present invention, the offset setting circuit sets a plurality of offsets (or offset values), and the offset switching means selectively selects one of the plurality of offsets.

In the configuration of the sensor control device according to the present invention, it is possible to make the different gas concentration detection ranges based on the offsets (or the offset values) by connecting disconnecting the offset setting circuit to/from the amplification circuit, or by changing the offsets in the offset setting circuit. It is thereby possible to set the optimum gas concentration detection ranges with different high concentration sides and different low concentration sides.

In accordance with another aspect of the present invention, there is provided a sensor control device for controlling a sensor element made up of a solid polymer electrolyte capable of detecting a concentration of a specific gas component in a target gas under a wide detection range. The sensor control device has a current detection resistance, an amplification circuit, an offset setting circuit, and an offset switching means. The current detection resistance detects a current flowing in the sensor element and generating an element current signal. The amplification circuit which is one of an inverting type and non-inverting type inputs the element current signal through one input signal terminal thereof, and amplifies the element current signal. The offset setting circuit sets an offset, which is connected to one of the input signal terminal for receiving the element current signal and the input signal terminal in the amplification circuit. The offset switching means switches the offset which is determined by the offset setting circuit according to the element current signal regarding the concentration of the specific gas component contained in the target gas.

In the sensor control device having the inverting or non-inverting type amplification circuit according to the present invention capable of amplifying the element current signal, it is possible to add the offset to the output signal of the amplification circuit by connecting one input signal terminal of the amplification circuit to the offset setting circuit. That is, the amplification circuit and the offset setting circuit forms the adding circuit. The output signal of the amplification circuit becomes the signal obtained by adding the offset, supplied from the offset setting circuit, to the element current signal corresponding to the magnitude of the current flowing in the sensor element. Or, the output signal from the amplification circuit is obtained by adding the offset value, supplied from the offset setting circuit, to a reference signal which is input to another input signal terminal of the amplification circuit, and is different from the input signal terminal for receiving the element current signal.

The configuration of the sensor control device having the single amplification circuit can set different gas concentration detection ranges. In this configuration, because the current value (namely, the offset value) to be supplied from the offset setting circuit to the amplification circuit is known in advance, it is particularly possible to detect the gas concentration of the target gas by adding the current value to the output signal of the amplification circuit.

On the contrary, in the relates art sensor control device using the differential amplification circuit (as a comparison example, see FIG. 14) instead of the inverting or non-inverting type amplification circuit, although the offset setting operation is performed by connecting the offset setting circuit to the one input signal terminal of the amplification circuit, the related art sensor control device (see FIG. 14, for example) has a possibility of fluctuating or varying the signal amplification factor and the gas concentration detection range, contrary to the expectation.

To use the inverting type or non-inverting type amplification circuit in the sensor control device of the present invention can avoid such a related-art drawback.

According to the present invention described above, it is possible to set one of the different gas concentration detection ranges and to perform the optimum gas concentration detection under each detection range.

In the sensor control device as another aspect of the present invention, it is preferable that the offset switching means switches or selects the offset determined by the offset setting circuit by connecting/disconnecting the one input signal terminal of the amplification means to/from the offset setting circuit. In the sensor control device as another aspect of the present invention, it is preferable that the offset setting circuit sets or selects a plurality of offset values, and the offset switching means selectively selects one of the plurality of offset values. According to each of the configurations of the sensor control device according to the present invention described above, it is possible to set the different offset values as the different gas concentration detection ranges for the target gas by connecting/disconnecting the offset setting circuit to/from the amplification circuit. This can easily set the different detection ranges having different high concentration sides and different low concentration sides.

The sensor control device according to the present invention is applicable as an air/fuel (A/F) detection device using the sensor element capable of detecting an air/fuel (A/F) ratio of an exhaust gas emitted from an internal combustion engine based on the element current signal detected by the sensor element. In the sensor control device according to the present invention, following detection ranges can be defined:

A stoichiometry detection range (as the stoichiometry zoom range RG2) for use in a stoichiometry combustion control, which is a part of the whole A/F ratio detection range detectable by the sensor element: and A lean detection range (as the lean zoom range RG3) for use in a lean combustion control, which is a part of the whole A/F ratio detection range detectable by the sensor element.

In the configuration of the sensor control device described above, the offset switching means judges whether the A/F ratio detection is performed under the stoichiometry detection range or the lean detection range according to the A/F ratio control. The offset switching means switches the offset according to the judgment result.

Each of the stoichiometry detection range and the lean detection range is a part of the whole detection range and has the detection range for a different A/F ratio. By switching the offset described above, it is possible to detect the optimum A/F ratio for each detection range. As a result, the sensor control device according to the present invention can efficiently perform the stoichiometry combustion control and the lean combustion control.

In the sensor control device as another aspect of the present invention, the A/F ratio detection rage (as the rich zoom range RG4) includes a rich detection range for use in a rich combustion control as a part of the whole A/F ratio detection range. The offset switching means selects one of the stoichiometry detection range, the lean detection range, and the rich detection range in order to detect the A/F ratio using the selected one, and switches the offset based on the judgment result.

The above configuration enables the sensor control device to perform the rich combustion control in addition to the stoichiometry combustion control and the lean combustion control. When the rich detection range is selected and used as the A/F ratio detection range, it is preferable to add the inverted offset, which is obtained by inverting the offset for use in the lean detection range, to the output of the amplification circuit. That is, when the lean detection range is used as the A/F ratio detection range, the current value corresponding to the offset is supplied from the offset setting circuit to the amplification circuit. On the contrary, when the rich detection range is used as the A/F ratio detection range, the current value corresponding to the offset is supplied from amplification circuit to the offset setting circuit.

In the sensor control device as another aspect of the present invention, it is preferable that each of the stoichiometry detection range, the lean detection range, and the rich detection range includes a stoichiometry value. Each detection range thereby includes the state in which the element current becomes zero (0 mA in the stoichiometry detection state). It is thereby possible to judge a circuit characteristic error based on variation of the output signal of the amplifier circuit when the sensor element is placed under the stoichiometry detection state.

It is concretely preferable that the sensor control device has a circuit characteristic detection means configured to detect a circuit characteristic error based on an output signal of the amplification circuit at the time when the current flowing in the sensor element is forcedly cut. For example, a voltage supply line to the sensor element is open in order to halt the supply of the voltage and to stop the element current flow. This case enables that the sensor control device and the sensor element are forcedly set in the stoichiometry detection state, and the presence of the circuit characteristic error of the amplification circuit is judged based on the variation of the output voltage of the amplification circuit.

The sensor control device as another aspect of the present invention further has a plurality of resistances for amplification and an amplification factor switching means. The plurality of resistances for amplification determines the amplification factors of the amplification circuit. The amplification factor switching means switches the resistances for amplification so that one of the resistances for amplification are used as an input resistance and the remaining resistances for amplification are used as a feedback resistance.

The sensor control device having the above configuration can adjust the gas concentration detection resolution by changeable setting the amplification factor (or a gain) of the amplification circuit. This can increase or improve the detection accuracy of the gas concentration of the target gas. The amplification factor of the amplification circuit can be changed by selecting the resistances as the input resistance and the feedback resistances in the resistances for amplification. This enables the sensor control device to have a simple circuit configuration when compared with the conventional sensor control device having a plurality of amplification circuits of different amplification factors. As described above, the present invention can provide the sensor control device having the improved or superior detection accuracy in a desired gas concentration range with a simple circuit configuration.

Considering the combination of the configuration described above, the sensor control device can set the gas concentration detection ranges having different ranges in addition to setting the gas concentration detection ranges under different offset setting states.

It is preferable to further have a switching element on the signal input line of an operational amplifier in the amplification circuit, and the resistances for amplification are switched according to the operation of the switching element. That is, because the signal input line of the operational amplifier has in general a high-impedance. Even if the switching element has a resistance component, it is possible to neglect the presence of the resistance component when the sensor control device has the configuration capable of changing the amplification factor by the switching element placed on the signal input line of a high impedance. Therefore the amplification circuit can amplify the signal with high accuracy.

In the sensor control device as another aspect of the present invention, the wide detection range for detecting the gas concentration of the target gas is divided into different detection ranges in advance. The amplification factor switching means switches the resistances for amplification so that the amplification factor of the amplification circuit is increased when the gas concentration of the specific gas component contained in the target gas is detected in a narrow detection range in the different detection ranges. The amplification factor switching means further switches the resistances for amplification so that the amplification factor of the amplification circuit is decreased when the gas concentration of the specific gas component contained in the target gas is detected in a wide detection range in the different detection ranges. In this configuration, the sensor control device using the relatively narrow detection range can performs the gas concentration detection of a high accuracy as a first or top priority in execution.

According to the present invention, when the sensor control device acts as the A/F ratio detection device and the target detection gas is an exhaust gas emitted from an internal combustion engine, it is preferable to perform the offset switching and the amplification factor switching under the following condition.

The sensor control device detects an A/F ratio of the exhaust gas in an A/F ratio detection range. The A/F ratio detection range is comprised of a whole A/F ratio detection range (as the whole detection range RG1), a stoichiometry detection range (as the stoichiometry zoom range RG2), and a lean detection range (as the lean zoom range RG3). The sensor element is detectable in the whole A/F ratio detection range. The stoichiometry detection range is a part of the whole A/F ratio detection range and for use in a stoichiometry combustion control. The lean detection range is a part of the whole A/F ratio detection range and for use in a lean combustion control.

Further, the sensor control device controls the following conditions (1) to (3). (1) The offset switching means does not give any offset to the amplification circuit when the sensor element detects the A/F ratio of the exhaust gas under the whole A/F ratio detection range. The amplification factor switching means selects the resistances for amplification so that the amplification factor is decreased. (2) The offset switching means does not give any offset to the amplification circuit when the sensor element detects the A/F ratio of the exhaust gas under the stoichiometry detection range, and the amplification factor switching means selects the resistances for amplification so that the amplification factor is increased. (3) The offset switching means gives an offset to the amplification circuit when the sensor element detects the A/F ratio of the exhaust gas under the lean detection range, and the amplification factor switching means selects the resistances for amplification so that the amplification factor is increased.

According to the configuration of the sensor control device, it is possible to easily switch or change the A/F ratio detection range to one of the whole detection range, the stoichiometry detection range, and the lean detection range. As a result, it is possible to efficiently execute the stoichiometry combustion control and the lean combustion control. In addition to this feature, it is possible to perform the sensor abnormal diagnosis and the like by detecting the ambient atmosphere.

In the sensor control device as another aspect of the present invention, it is possible to further define a rich detection range (as the rich zoom range RG4), which is a part of the whole A/F ratio detection range, for use in a rich combustion control. When the sensor element detects the A/F ratio of the exhaust gas under the rich detection range, it is preferable that the offset switching means gives an inverted offset to the amplification circuit, where the inverted offset is obtained by inverting the offset for use in the lean detection range. The amplification factor switching means increases the amplification factor. It is thereby possible to perform the rich combustion control in addition to the stoichiometry combustion control, and the lean combustion control.

In the sensor control device as another aspect of the present invention, the amplification circuit comprises one of a constant current source and a pull-down resistance at an output stage thereof. In this configuration, it is possible to expand the range of the output voltage of the amplification circuit toward the lower limit side with a simple configuration. That is, the expansion of the range of the output voltage provided from the amplification circuit can be realized with an amplifier of a small sized chip area. This can reduce the size of the sensor control device.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
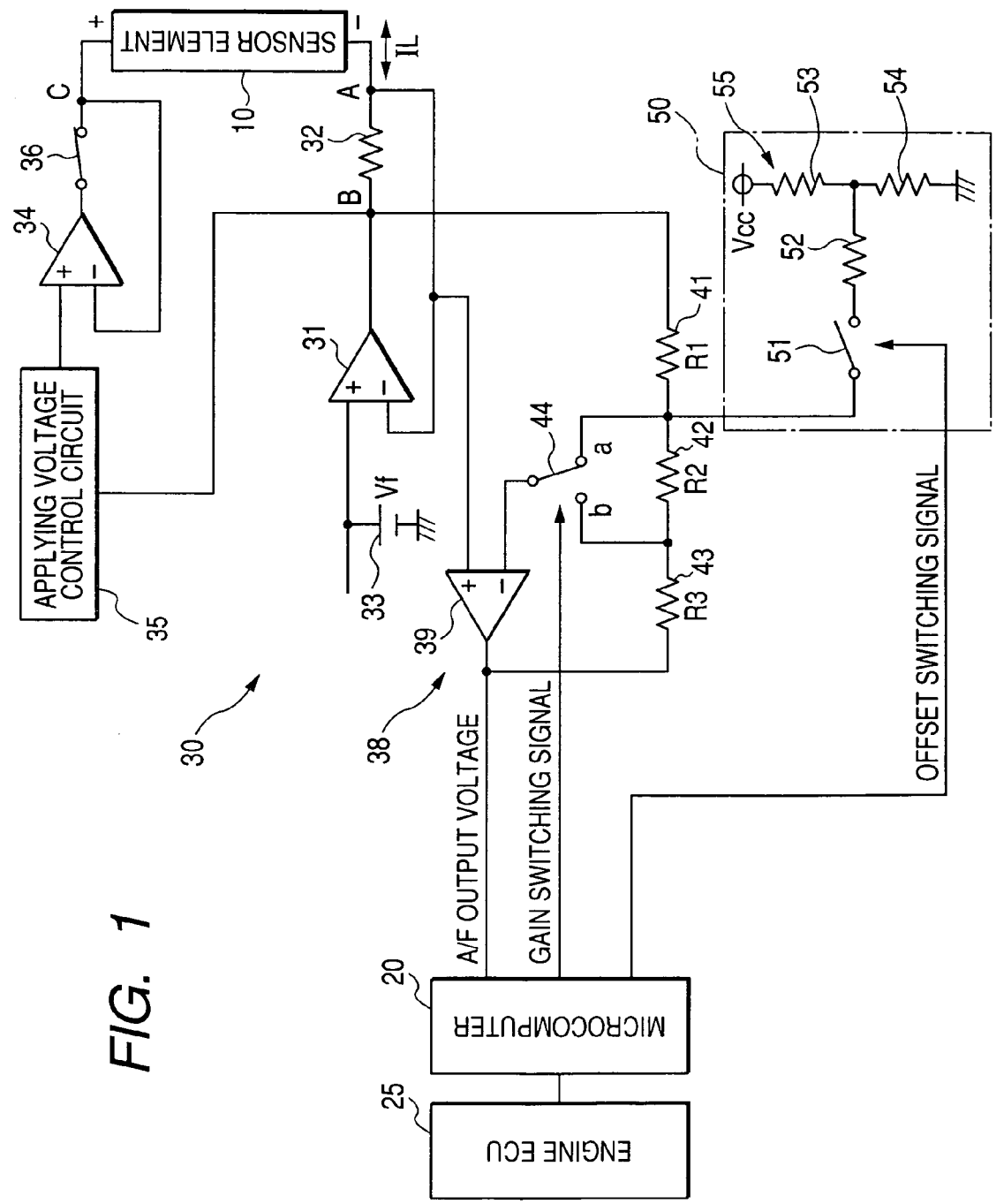
FIG. 1 shows a circuit configuration of a sensor control device equipped with a sensor element according to a first embodiment of the present invention.

Hereinafter, various embodiments of the present invention will be described with reference to the accompanying drawings. In the following description of the various embodiments, like reference characters or numerals designate like or equivalent component parts throughout the several diagrams.

First Embodiment

A description will be given of the sensor control device according to the first embodiment of the present invention with reference to diagrams.

The sensor control device 30 according to the first embodiment acts as an air/fuel (A/F) ratio detection device and further applied to an A/F ratio control system equipped with an electric control unit (ECU) for controlling the operation of an internal combustion engine (which will be referred to as the "engine" for short) mounted on a motor vehicle. The A/F ratio detection device is capable of detecting an oxygen concentration in an exhaust gas (or a combustion gas) as a target gas emitted from the engine. The ECU in the A/F ratio control system for the engine control receives the detection result regarding the A/F ratio transferred from the sensor control device 30 equipped with the sensor element 10.

FIG. 1 shows a circuit configuration of the sensor control device 30 in the A/F ratio control system according to the first embodiment of the present invention. The A/F ratio control system can execute, as necessary, the stoichiometry combustion control for carrying out the feedback control of the A/F ratio near the stoichiometry value and the lean combustion control for carrying out the feedback control of the A/F ratio in the lean area.

The A/F ratio control system equipped with the sensor control device according to the present invention can detect the A/F ratio in a wide range from a fuel rich zone (for example, A/F11) to an atmosphere condition in order to control various conditions such as a wide range A/F ratio control corresponding to recent or future automobile emission control and on-board diagnostics (or OBD), fuel-rich combustion control when the engine operates in a fuel rich combustion, NOx discharging control for NOx storage reduction catalyst (NSR) placed in an exhaust gas pipe, and a sulfur poisoning elimination control and the like.

First of all, a description will now be given of the configuration of the A/F sensor incorporated in the sensor control device according to the first embodiment of the present invention with reference to FIG. 2.

The A/F sensor has a sensor element 10 of a lamination or multi-layer configuration. FIG. 2 is a sectional view of the A/F sensor 10.

Figure 2:
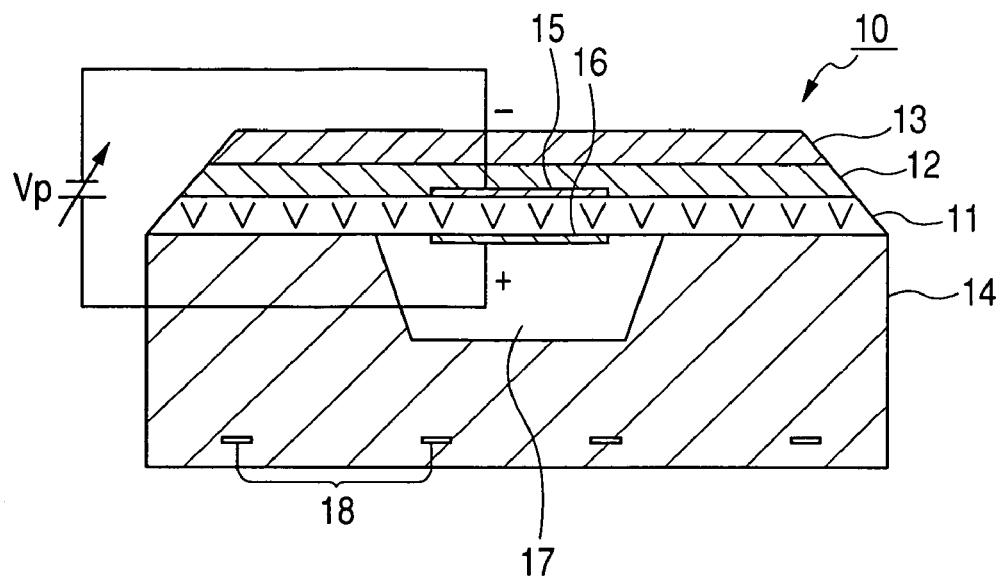
FIG. 2 is a sectional view of an A/F sensor in the sensor element shown in FIG. 1.

The actual sensor element 10 has a longitudinal shape along a vertical direction in FIG. 2. A housing or an element cover accommodates the entire of the sensor element 10 therein. The sensor element 10 is composed mainly of a solid polymer electrolyte layer 11, a diffusion resistance layer 12, a shielding layer 13, and an insulation layer 14 which are laminated, as shown in FIG. 2.

The sensor element 10 is covered with a protection layer (omitted from FIG. 2). The solid polymer electrolyte layer 11 of a rectangle plate shape is a sheet made up of zirconia (zirconia dioxide $ZrO_2$) of a partially stable condition. Electrodes 15 and 16 form a pair of electrodes and are formed on both end surfaces of the solid polymer electrolyte layer 11. Those electrodes 15 and 16 face to each other through the solid polymer electrolyte layer 11.

The diffusion resistance layer 12 is composed of porous sheet through which the exhaust gas emitted from the engine mounted on a motor vehicle is introduced into the electrode 15. The shielding layer 13 is made up of a compact layer in order to suppress the permeation of the exhaust gas. Although each layer 12 and 13 is made from alumina, spinel, and zirconia by sheet molding, each layer 12 and 13 has a different gas permeability obtained by different average size and pore ratio of porosity.

The insulation layer 14 is made from a high thermal conduction ceramics such as alumina. An ambient atmosphere duct is formed at a part of the insulation layer 14 facing the electrode 16. A plurality of heaters 18 are also embedded in the insulation layer 14. Those heaters 18 are made of heating element capable of generating heat energy on receiving an electric power from a battery power source (not shown). The entire of the sensor element 10 is heated by the heat energy of the heaters 18 embedded in the insulation layer 14.

In the sensor element 10 having the configuration described above, the exhaust gas is introduced through a side of the diffusion resistance layer 12 in the sensor element 10 and the exhaust gas reaches the electrode 15. When the sensor element 10 introduces a fuel lean exhaust gas, oxygen contained in the exhaust gas is decomposed at the electrode 15, and the exhaust gas is emitted to an atmosphere duct 17 at the electrode 16. When the sensor element 10 introduces a rich exhaust gas, oxygen is decomposed at the electrode 16 in the atmosphere duct 17, and the exhaust gas is discharged through the electrode 15 to the exhaust gas side.

Figure 3:
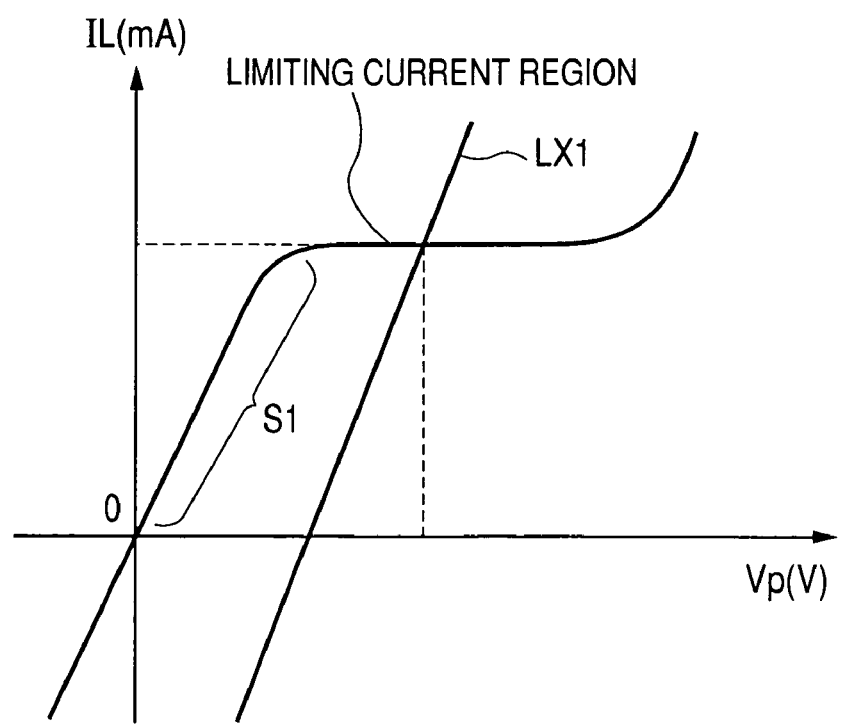
FIG. 3 shows a voltage-current characteristic (Vp-IL characteristic) of the A/F sensor shown in FIG. 2.

FIG. 3 shows a voltage-current characteristic (Vp-IL characteristic) of the A/F sensor 10 shown in FIG. 2. In FIG. 3, the straight line part, which is approximately parallel to the Voltage (Vp(V)) axis (as the horizontal axis), is a limiting current area (designated by LC in FIG. 3) which specifies the magnitude of an element current IL (as a limiting current) of the sensor element 10. Increasing and decreasing of the element current IL (mA) corresponds to the increasing and decreasing of the A/F ratio (that is, corresponds to the degree of a lean state and a rich state). When the A/F ratio is more shifted toward the lean state, the element current IL is more decreased. Reference character LX1 in FIG. 3 designates an applying voltage straight line (or an applying voltage characteristic) by which the magnitude of the applying voltage Vp to be applied to the sensor element 10 is determined. In FIG. 3, the slant of the applying voltage straight line LX1 approximately corresponds to the slant of the resistance controlling area (which is the slant area S1 at a low voltage side observed from the limiting current area LC).

Next, a description will now be given of the electric configuration of the sensor control system as a main part of the present invention with reference to FIG. 1.

As shown in FIG. 1, the sensor control system is composed mainly of an engine ECU 25, a microcomputer 20 and the sensor control device 30. The sensor control system shown in FIG. 1 measures the element current which flows in the A/F sensor (having the sensor element 10) and then calculates an A/F value based on the measured element current.

The microcomputer 20 is composed mainly of a CPU (a central processing unit), various types of memories, A/D (analogue/digital) converters and the like, which is well known and easily available in a market. In particular, the A/D converter has a capability of 10 bit resolution, for example, and whose operating voltage is within a range of 0 to 5 Volts. The microcomputer 20 always calculates the A/F value and successively transfers the calculated one to the engine ECU 25.

The engine ECU 25 performs various functions such as a stoichiometry feedback control, a lean feedback control, a rich feedback control when the amount of fuel supplied to the engine is increased during a high load of the engine, and an on-board diagnostics (or OBD) for detecting a sensor abnormal state under an atmosphere state of decreasing the amount of fuel. The engine ECU 25 performs those functions based on the A/F value obtained from the A/F sensor having the sensor element 10.

In a concrete example of the stoichiometry feedback control, a target air-fuel (A/F) ratio is set to stoichiometry (A/F=14.7), and the engine ECU 25 controls the fuel injection amount of an injector so that the actual A/F ratio detected by the A/F sensor becomes equal to the target A/F ratio (which will be referred to as the "precision stoichiometry control").

In a concrete example of the lean feedback control, a target lean A/F ratio (for example, A/F=30.0) is set, and the engine ECU 25 controls the fuel injection amount of the injector so that the actual A/F ratio detected by the A/F sensor becomes equal to the target lean A/F ratio (which will be referred to as the "precision lean combustion control").

Further, in a concrete example of the rich feedback control, a target rich A/F ratio (for example, A/F=10.0) is set when the vehicle has a high load such as the accelerating time and the time when the vehicle runs on an uphill slope, and the engine ECU 25 controls the fuel injection amount of the injector so that the actual A/F ratio detected by the A/F sensor becomes equal to the target rich A/F ratio.

Still further, in a concrete example of the sensor abnormal diagnosis control when the fuel supply to the engine is halted, the engine ECU 25 judges the occurrence of deterioration of the A/F sensor based on whether or not the output value (as an element current value) of the A/F sensor becomes the value corresponding to the atmosphere condition when the gas condition in the exhaust gas pipe becomes the atmosphere (that is, an already-known atmosphere) caused by cutting the fuel supply to the engine.

The stoichiometry feedback control and the lean feedback control need to detect the precision A/F ratio in the area near the stoichiometry value and in a desired lean control region. On the contrary, the rich feedback control and the sensor abnormal diagnosis need to detect the A/F ratio in a wide range from the rich region to a super lean region (the atmosphere condition).

The A/F ratio control system including the sensor control device according to the first embodiment of the present invention prepares following three types of A/F ratio detection ranges RG1, RG2, and RG3 and selects the optimum A/F ratio detection range according to the type of the A/F ratio control to be carried out.

The whole range RG1 is a range from the rich region to the super lean region (atmosphere). The stoichiometry zoom range RG2 is the area near the stoichiometry value. The lean zoom range RG3 is a predetermined lean detection range.

The whole range RG1 corresponds to the whole range which is detectable by the sensor element 10. The stoichiometry zoom range RG2 is a part of the whole range RG1 (as the whole A/F ratio range) and corresponds to the stoichiometry detection range for use in the stoichiometry combustion control. The lean zoom range RG3 is a part of the whole range RG1 (as the whole A/F ratio range) and corresponds to the lean detection range for use in the lean combustion control.

Figure 4:
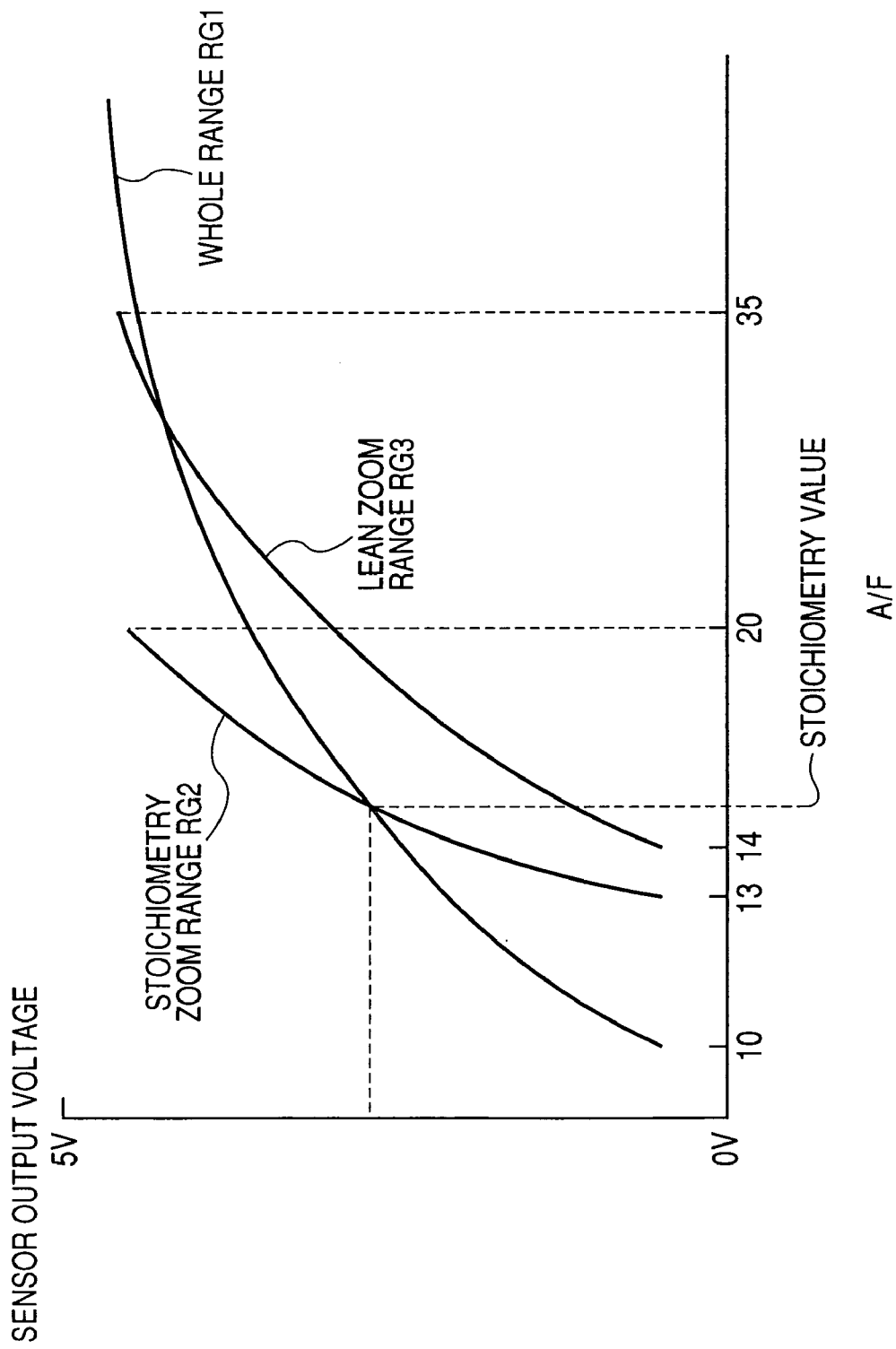
FIG. 4 shows a relationship between the A/F ratio and a sensor output voltage in various types of ranges RG1, RG2, and RG3.

FIG. 4 shows a relationship between the A/F ratio and a sensor output voltage in the three types of the A/F ratio detection ranges RG1 to RG3. The range of the A/F output voltage is defined according to the A/D processing range of the A/D converter in the microcomputer 20. As clearly shown in FIG. 4, the A/F output voltage is within a range of approximately 0V to 5V.

As shown in FIG. 4, the whole range RG1 is set within a range of A/F ratio=10 to atmosphere. The stoichiometry zoom range RG2 is set within a range of A/F ratio=13 to 20. The lean zoom range RG3 is set within a range of A/F ratio=14 to 35. Each of those ranges RG1 to RG3 is set as the detection range covering the stoichiometry value. The A/F ratio detection using the whole range RG1 can detect the A/F ratio in the whole range which is defined as the operation range of the A/F ratio control system.

The A/F ratio detection in the stoichiometry zoom range RG2 and the lean zoom range RG3 can enhance the detection resolution of the A/F ratio in a limited voltage range (within the A/D operational voltage in the microcomputer 20).

Figure 5:
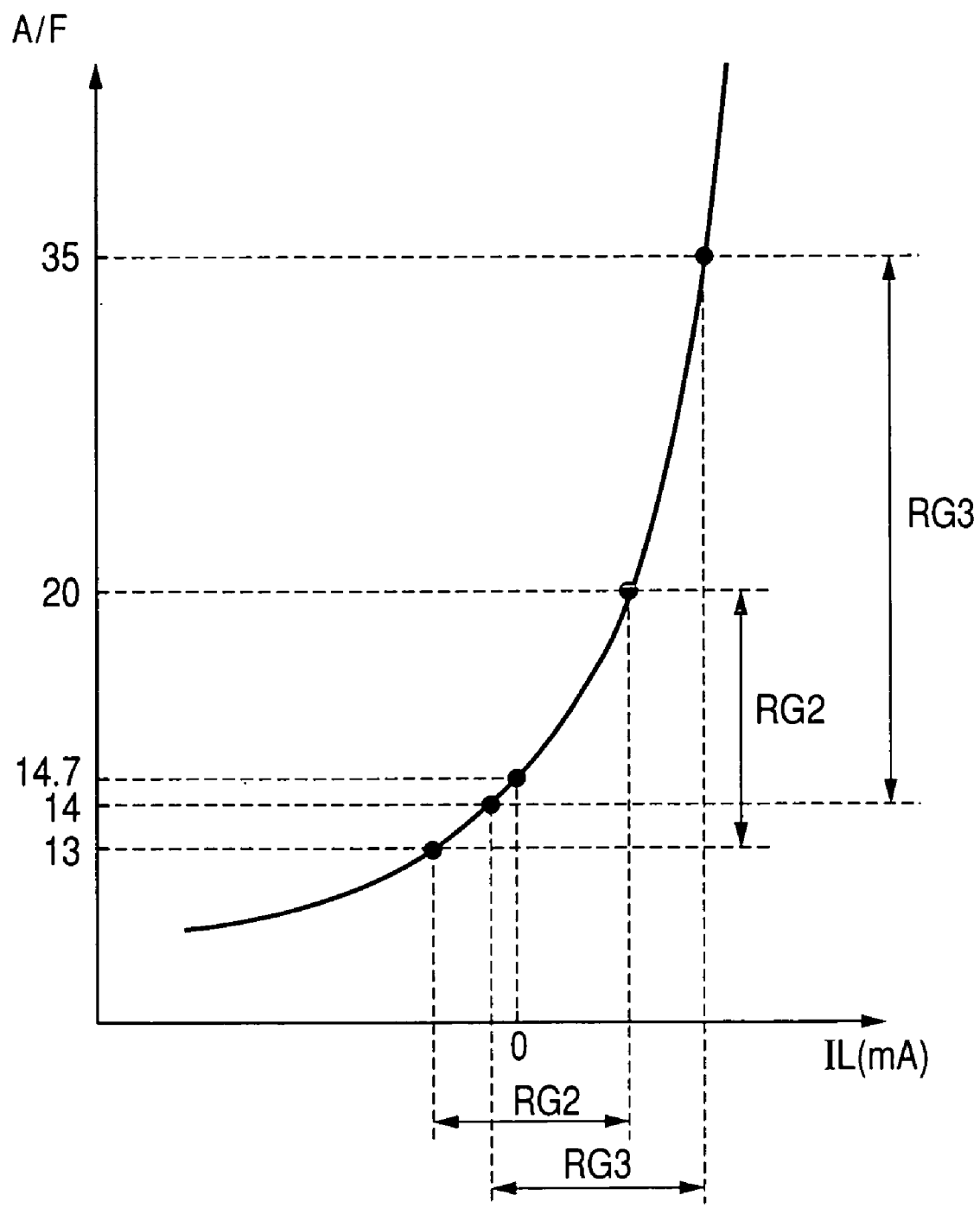
FIG. 5 shows a relationship between the A/F sensor and an element current IL which flows through the A/F sensor.

FIG. 5 shows a relationship between the A/F output voltage and an element current IL (mA) flowing through the A/F sensor 10. As shown in FIG. 5, the element current IL has 0 mA at the stoichiometry value (A/F ratio=14.7).

When the lean region is compared with the rich region, they have different A/F sensitivity to the element current IL. The former (the lean range) has a high A/F sensitivity. This depends on the sensitivity characteristic of the sensor element 10. In this case, even if the element current range (IL width in the horizontal axis in FIG. 5) is same in both the stoichiometry zoom range RG2 and the lean zoom range RG3, it can be recognized that they have different actual A/F ratio detection range (as the width of the A/F output voltage in the vertical axis in FIG. 5).

The A/F ratio control system equipped with the sensor control device of the first embodiment performs the A/F ratio control with the same element current range (in other words, the range of the A/F output voltage) of both the stoichiometry zoom range RG2 and the lean zoom range RG3, but with different actual air/fuel detection ranges.

The A/F ratio control system equipped with the sensor control device does not perform the stoichiometry feedback control, the lean feedback control, and the sensor abnormal diagnosis, simultaneously, that is, the A/F ratio control system selectively performs each control. Accordingly, there is not necessary to perform the A/F ratio detection in the stoichiometry zoom range RG2 and the lean zoom range RG3 simultaneously. The A/F ratio control system equipped with the sensor control device selectively selects the optimum A/F ratio detection range from those ranges RG1, RG2, and RG3, and performs the A/F ratio detection (the calculation of the A/F value) in the selected range.

Returning to FIG. 1, in the sensor control device 30 of the first embodiment, an negative (−) terminal of the sensor element 10 is connected to a reference voltage power source 33 through an operational amplifier 31 and a current detection resistance 32 (as a resistance for measuring the current), and the positive (+) terminal of the sensor element 10 is connected to an applying voltage control circuit 35 through an operational amplifier 34. The output terminal of the operational amplifier 34 is connected to a switch 36. The switch 36 acts as a current breaking means for breaking the supply of the current flowing in the sensor element 10. The switch 36 is closed in a normal state and becomes open when receiving the open-instruction signal transferred from the microcomputer 20.

In this case, the voltage potential of the node A as one end terminal of the current detection resistance 32 is kept to the reference voltage Vf. The element current IL flows in the current detection resistance 32. The voltage potential at the node B is changed according to the magnitude of the element current IL. For example, when the exhaust gas is lean, the voltage potential at the node B drops because the current flows from the positive (+) terminal to the negative (−) terminal of the sensor element 10. On the contrary, when the exhaust gas is rich, the voltage potential at the node B is increased because the current flows from the negative (−) terminal to the positive (+) terminal of the sensor element 10.

The applying voltage control circuit 35 monitors the voltage potential at the node B and determines the applying voltage to be applied to the sensor element 10 according to the voltage detected at the node B. (For example, the applying voltage control circuit 35 detects the magnitude of the voltage to be applied according to the applying voltage straight line LX1 shown in FIG. 3.)

The applying voltage control circuit 35 controls the voltage at the node C through the operational amplifier 34. When the A/F detection is performed near the stoichiometry value, it is possible to fix the applying voltage to be applied to the sensor element 10.

An inverting amplification circuit 38 is connected to the nodes A and B at the both ends of the current detection resistance 32. The A/F output voltage as the output of the inverting amplifier circuit 38 is input to the A/D input terminal of the microcomputer 20. The microcomputer 20 receives the A/F output voltage and calculates the A/F value based on the received one. The inverting amplifier circuit 38 is composed mainly of an operational amplifier 39, three resistances 41, 42, and 43 for amplification connected in series, and a switching element 44 made up of a MOS transistor, for example. In the first embodiment, the resistances 41, 42, and 42 for amplification have resistance values R1, R2, and R3, respectively.

The element current signal detected by the current detection resistance 32 is input to the negative (−) input terminal of the operational amplifier 39 forming the inverting amplifier circuit 38.

A switching element 44 is placed on the signal input line connected to the negative (−) input terminal (or an inverting input terminal) of the operational amplifier 39. Contacts "a" and "b" to be selectively connected by the switching element 44 are connected to both end terminals of the resistance 42 for amplification at the middle position in the three resistances 41, 42, and 43. The negative input terminal of the operational amplifier 39 is connected to the contact a by the switching element 44.

When receiving a gain switching signal generated by and transferred from the microcomputer 20, the switching element 44 performs the switching operation to connect the negative input terminal of the operational amplifier 39 to the contact b.

In the condition where the negative input terminal of the operational amplifier 39 is connected to the contact a (see FIG. 1), the resistance 41 for amplification becomes an input resistance for the inverting amplifier circuit 38, and the resistances 42 and 43 for amplification become feedback resistances for the inverting amplifier circuit 38. In this condition, an amplification factor GA of the inverting amplifier circuit 38 can be expressed by the following equation (1).

$$GA=(R2+R3)/R1 \quad (1).$$

In the condition in which the negative input terminal of the operational amplifier 39 is connected to the contact b of the switching element 44, the resistances 41 and 42 for amplification become input resistances for the inverting amplifier circuit 38, and the resistance 43 for amplification becomes a feedback resistance for the inverting amplifier circuit 38. In this condition, an amplification factor GB of the inverting amplifier circuit 38 can be expressed by the following equation (2).

$$GB=R3/(R1+R2) \quad (2).$$

The comparison result of the above amplification factors GA and GB provides the relationship GA>GB. That is, when the switching element 44 connected to the negative input terminal of the operational amplifier 39 selects the contact a, it can be considered to have a relatively high amplification factor. On the contrary, when the switching element 44 connected to the negative input terminal of the operational amplifier 39 selects the contact b, it can be considered to have a relatively low amplification factor. Accordingly, the high amplification factor is switched to the low amplification factor of the inverting amplifier circuit 38 by switching the contact a to the contact b of the switching element 44. In the first embodiment of the present invention, the amplification factor GA becomes "×15" when the switching element 44 selects the contact a as one conducting node, and the amplification factor GB becomes "×5" when the switching element 44 selects the contact b as another conducting node.

Considering the A/F ratio detection ranges described above, when the A/F ratio control system performs the A/F ratio detection in the relatively narrow detection range such as the stoichiometry zoom range RG2 and the lean zoom range RG3, it is preferred to increase the amplification factor of the inverting amplifier circuit 38 in order to increase the detection resolution. This control can be achieved by selecting the contact a of the switching element 44 in order to connect the operational amplifier 39 and the offset setting circuit 50.

On the contrary, when the A/F ratio control system performs the A/F ratio detection in the relatively wide detection range such as the whole range RG1, it is preferred to decrease the amplification factor of the inverting amplifier circuit 38 in order to expand the detection range. This control can be achieved by selecting the contact b of the switching element 44 connected to the operational amplifier 39 in order to connect the operational amplifier 39 and the offset setting circuit 50.

In this case, the microcomputer 20 receives information regarding the A/F ratio control which is transferred from the engine ECU 25, and generates and outputs a gain switching signal to the switching element 44 based on the received information. Thus, the switching operation of the amplification factor of the inverting amplifier circuit 38 corresponding to the A/F ratio detection range can be carried out.

As shown in FIG. 1, an offset setting circuit 50 is connected to the middle node between the resistances 41 and 42 for amplification. The offset setting circuit 50 applies an offset to the A/F output voltage as the output of the inverting amplifier circuit 38. The A/F ratio detection range is changed by the offset transferred from the offset setting circuit 50.

Both the inverting amplifier circuit 38 and the offset setting circuit 50 form an addition circuit. The inverting amplifier circuit 38 outputs the A/F output voltage as the voltage signal obtained by adding the offset signal to the element current signal corresponding to the magnitude of the element current IL of the sensor element 10.

The offset setting circuit 50 is composed of the switching element 51, a resistance 52 connected in series to the switching element 51, and a power source 55 having a pair of dividing voltage resistances 53 and 54. The switching element 51 is composed of a MOS transistor, for example. The switching element 51 performs ON/OFF operation based on the offset switching signal transferred from the microcomputer 20.

In the offset setting circuit 50 having such a configuration, when receiving the offset switching signal of a low level, the switching element 51 is fallen into OFF state. This state breaks the connection between the inverting amplifier circuit 38 and the offset setting circuit 50. Therefore the inverting amplifier circuit 38 operates regardless of the operation of the offset setting circuit 50. That is, this condition provides that the A/F output voltage is free from the offset operation of the offset setting circuit 50.

On the contrary, when receiving the offset switching signal of a high level, the switching element 51 is turned ON. Accordingly, the inverting amplifier circuit 38 is connected to the offset setting circuit 50 through the switching element 51. The inverting amplifier circuit 38 operates in the condition obtained by reflecting the offset transferred from the offset setting circuit 50. That is, the offset current determined by the resistance 52 and the electrical power source 55 flows into the inverting amplifier circuit 38. The offset is obtained according to the offset current, and the offset is added to the A/F output voltage output from the inverting amplifier circuit 38.

Considering the A/F ratio detection range described above, when the A/F ratio detection is performed in the stoichiometry zoom range RG2, the switching element 51 becomes OFF, and as shown in FIG. 4 and FIG. 5, the A/F ratio detection range round the stoicimetry can be achieved. This operation in the stoichiometry zoom range RG2 is the same as that in the whole range RG1.

When the A/F ratio detection is performed in the lean zoom range RG3, the switching element 51 is turned OFF, and as shown in FIG. 4 and FIG. 5, the A/F ratio detection range in a predetermined lean range can be achieved.

Figure 6:
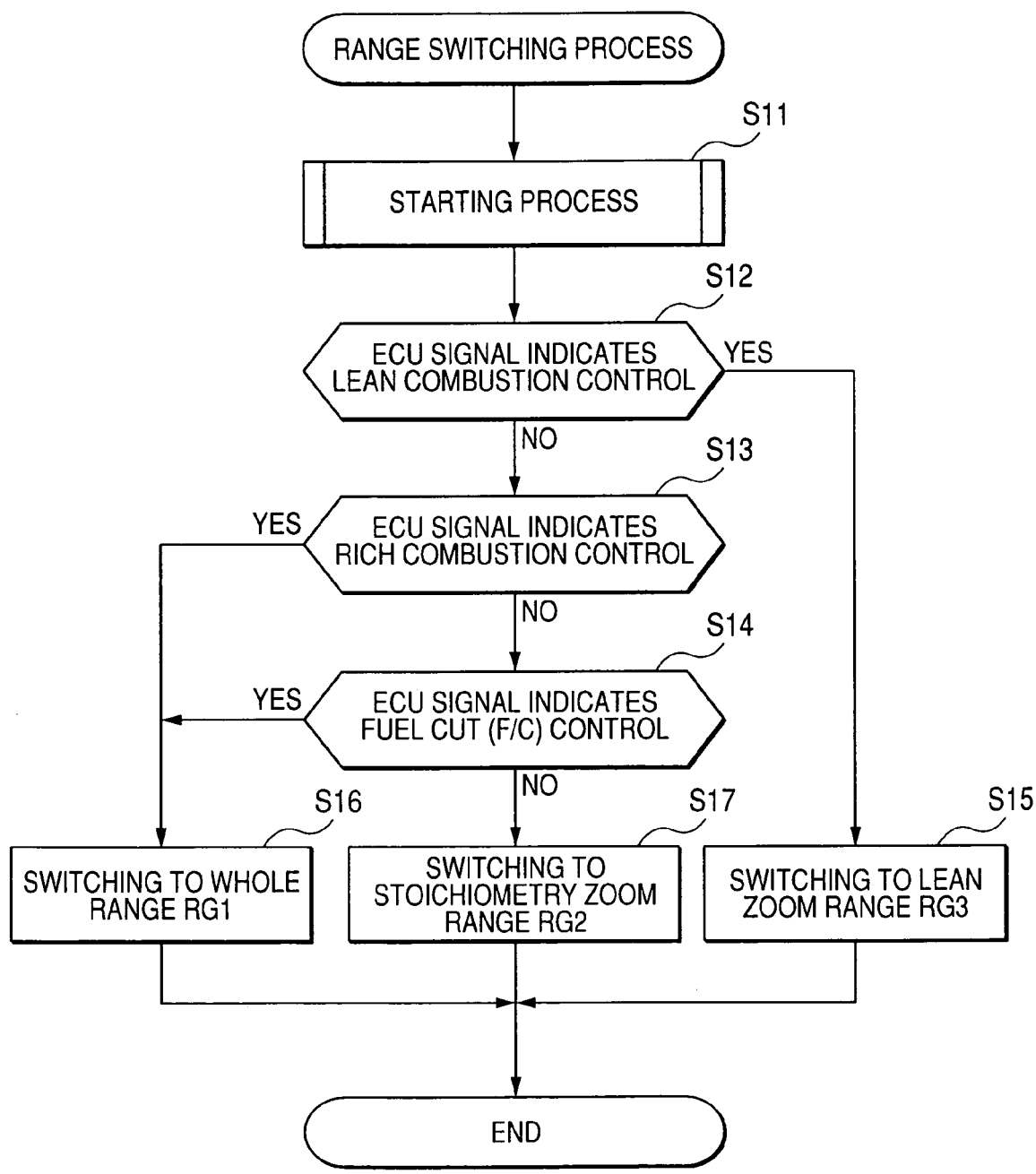
FIG. 6 is a flow chart showing a range switching process performed by the A/F ratio detection system equipped with the sensor control device according to the first embodiment of the present invention.

Next, a description will now be given of an actual switching procedure for the A/F ratio detection range by the A/F ratio detection system with reference to FIG. 6. FIG. 6 is a flow chart showing the starting process of switching the A/F ratio detection range performed by the A/F ratio detection system equipped with the sensor control device according to the first embodiment of the present invention.

The microcomputer 20 repeatedly performs the process of switching the A/F ratio detection range at a predetermined interval of time.

In FIG. 6, the starting process is performed at step S11. The starting process in step S11 is carried out once when the engine starts. The detailed explanation of step S11 will be explained later with reference to FIG. 7.

After step S11, the engine control state is judged each occasion in steps S12 to S14. That is, in step S12, it is judged whether or not the ECU signal transferred from the engine ECU 25 is the signal indicating the lean combustion control or not. For example, the lean combustion control is performed in a low load driving when the motor vehicle runs at a constant speed on an express way or a superhighway. In this case, "YES" in the step S12 is selected, and the operation flow goes to step S15.

In step S13, it is judged whether or not the ECU signal indicates the rich combustion control. In step S14, it is judged whether or not the ECU signal indicates the current state is in the fuel cutting (F/C) control. When the detection result in step S13 indicates that the ECU signal indicates the rich combustion control ("YES" in step S13) or the detection result in step S14 indicates that the ECU signal indicates the F/C control ("YES" in step S14), the operation flow goes to step S16. On the contrary, when "NO" is selected in all steps S12, S13, and S14, the microcomputer 20 judges that the current control is the stoichiometry combustion control, and the operation flow goes to step S17.

In step S15, the lean zoom range RG3 is selected as the A/F ratio detection range. In a concrete operation, the switching element 44 for the inverting amplifier circuit 38 is switched to the contact a, and the switching element 51 in the offset setting circuit 50 is turned ON. (If the same condition has been obtained, the same condition is maintained. Hereinafter, step S16 and step S17 will be performed with the same manner.) Thereby, the lean zoom range RG3 is set as the A/F ratio detection range with a relatively high amplification factor under the condition of adding the offset.

In step S16, the whole range RG1 is set as the A/F ratio detection range. In a concrete operation, the switching element 44 for the inverting amplifier circuit 38 is switched to the contact b, and the switching element 51 in the offset setting circuit 50 is turned OFF. Thereby, the whole range RG1 is set as the A/F ratio detection range with a relatively low amplification factor under the condition of not adding any offset.

In step S17, the stoichiometry range RG2 is set as the A/F ratio detection range. In a concrete operation, the switching element 44 for the inverting amplifier circuit 38 is switched to the contact a, and the switching element 51 in the offset setting circuit 50 is turned OFF. Thereby, the stoichiometry zoom range RG2 is set as the A/F ratio detection range with a relatively high amplification factor under the condition of not adding any offset.

The switching condition for selecting each of those ranges RG1, RG2, and RG3 described above is not limited by the use of the conditions described above (step S12 to step S14). It is also possible to use other conditions.

Figure 7:
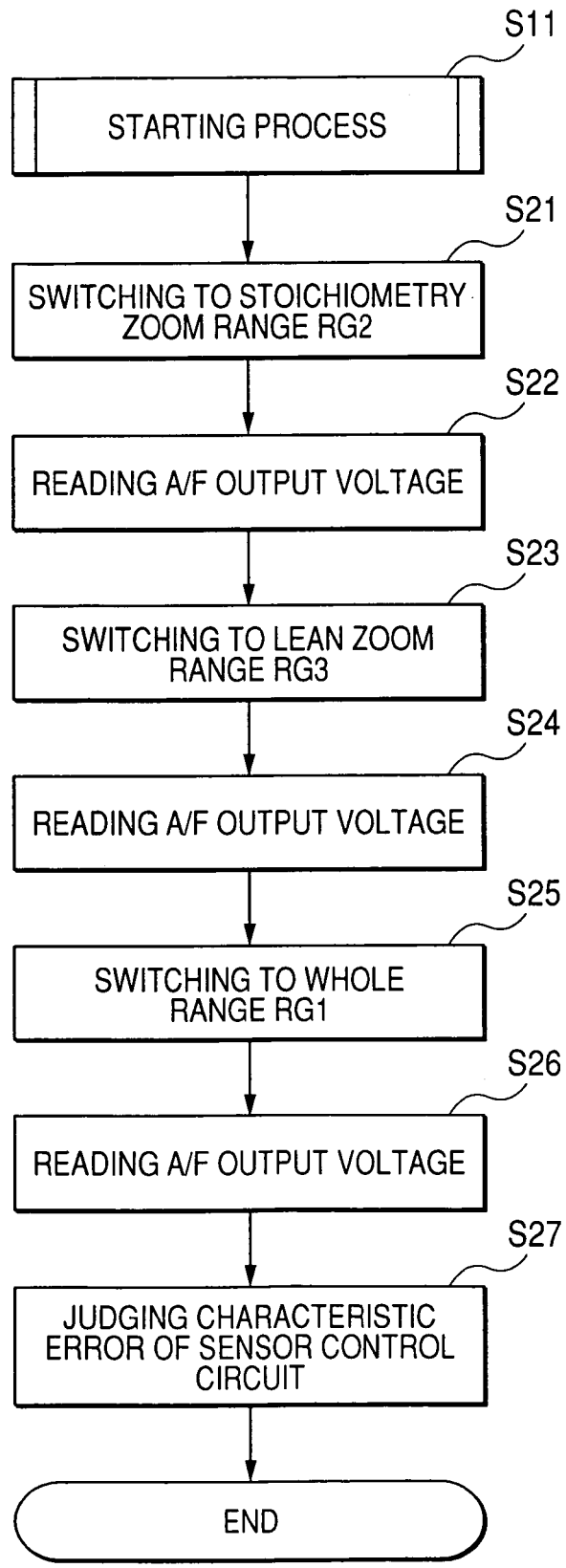
FIG. 7 is a flow chart showing a starting process which is carried out once by the A/F ratio control system when the engine starts.

FIG. 7 is a flow chart showing the starting process in step S11 (see FIG. 6) in detail. The sensor control system executes the starting process in step S11 once when the engine starts.

The starting process at step S11 (including step S21 to step S27) judges the presence of a characteristic error of the sensor control device 30, as shown in FIG. 6 and FIG. 7.

In a concrete example, the ranges RG1, RG2, and RG3 are switched under the condition in which no current (as the element current) is supplied to the sensor element 10 (obtained by opening the switch 36 shown in FIG. 1). The characteristic error of each range RG1 to RG3 is detected based on the A/F output voltage such a condition. In more detail, the characteristic error is diagnosed whether or not the A/F output voltage becomes the value corresponding to the element current IL=0 mA.

Hereinafter, the operation procedure when the engine starts will be explained in detail.

In step S21 of FIG. 7, the current range is switched to the stoichiometry zoom range RG2. In step S22 following step S21, the microcomputer 20 reads the A/F output voltage output from the amplifier 39 under the stoichiometry zoom range RG2. In step S23, the current range is switched to the lean zoom range RG3. In step S24 following step S23, the microcomputer 20 reads the A/F output voltage output from the amplifier 39 under the lean zoom range RG3.

In step S25, the current range is switched to the whole range RG1. In step S26 following step S25, the microcomputer 20 reads the A/F output voltage from the amplifier 39 under the whole range RG1.

Finally, in step S27, each A/F output voltage obtained at each step S22, S24, and S26 is compared with an abnormal judgment value (which is the value corresponding to the element current IL=0 mA). The microcomputer 20 judges the characteristic error of the sensor control device 30 based on the judgment results obtained by the above procedure.

Because the stoichiometry zoom range RG2 and the whole range RG1 do not use any offset value, there is a correlation in characteristic error. Therefore the characteristic error of one range can be obtained from the characteristic error of the other range. Accordingly, it is possible to skip or omit steps S21 and S22 or steps S25 and S26 in operation. For example, when the characteristic error of the whole range RG1 is obtained based on the characteristic error in the stoichiometry zoom ranger RG2, it is possible to obtain the characteristic error in the whole range RG1 by multiplying the characteristic error in the stoichiometry zoom range RG2 by a ratio of the amplification factors of those ranges RG1 and RG2. The abnormal diagnosis process described above can be carried out at the time other than the engine starting time, for example, during the driving of or the stop of the motor vehicle.

The sensor control device 30 and the A/F ratio control system according to the first embodiment of the present invention have the following superior effects.

It is possible to switch the stoichiometry zoom range RG2 and the lean zoom range RG3 by performing the connection/disconnection of the offset setting circuit 50 to the one input signal terminal of the operational amplifier 39 in the inverting amplification circuit 38. In this case, in the lean zoom range RG3 of adding the offset, because the magnitude of the current to be added flowing into the operational amplifier 39 from the offset setting circuit 50 is known in advance, it is possible to preciously detect the A/F ratio using the current value to be added.

Figure 14:
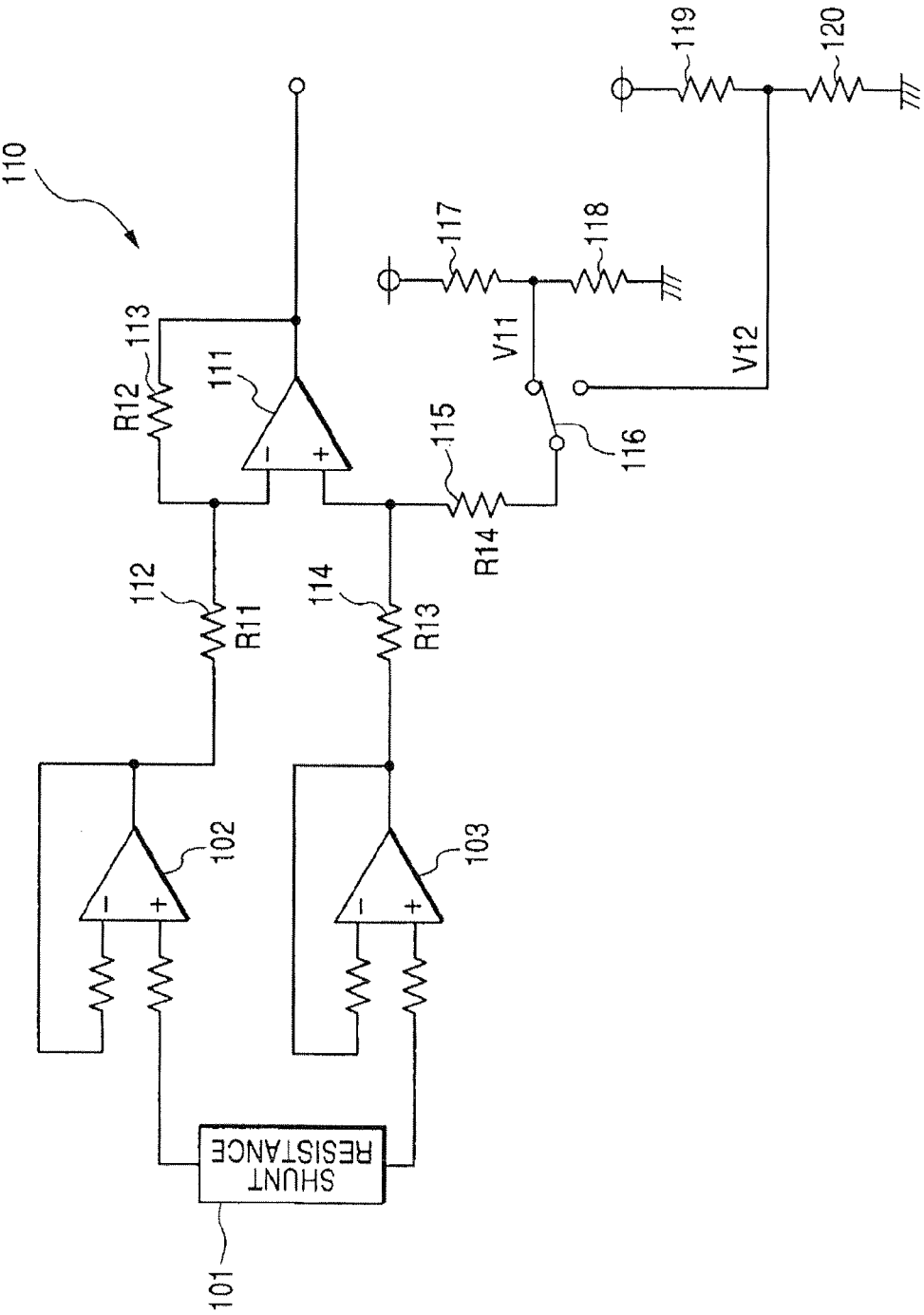
FIG. 14 is a circuit diagram showing a conventional sensor control device.

According to the configuration using the inverting amplification circuit 38 as the amplifier for amplifying the element current, it is possible to avoid or solve the problem that the signal amplification ratio or the A/F ratio detection range is varied or fluctuated, contrary to expectation, when compared with the case using the differential amplifier (in the related art technique shown in FIG. 14). In addition, the related art configuration using the differential amplifier shown in FIG. 14 needs to add the buffers 102 and 103 through which the signal is transferred to both the end terminals of the operational amplifier 111. On the contrary, the configuration of the sensor control device according to the first embodiment does not need to have any buffer. This can provide the sensor control device such as the A/F sensor control device with simple configuration.

Further, according to the first embodiment, the element current IL flowing in the current detection resistance 32 is detected at the middle node B in FIG. 1 between the operational amplifier 31 and the current detection resistance 32. This configuration can halt the flow of the feedback current from the output terminal of the operational amplifier 39 to the current detection resistance 32 through the resistances 41 to 43 for amplification. (That is, in this case, the feedback current flows into the operational amplifier 32 through the node B shown in FIG. 1.) The case of flowing the current into the current detection resistance 32 needs to add a buffer and the like on the signal input line for the operational amplifier 39 in order to suppress decreasing the detection accuracy of the element current flowing through the sensor element 10. However, the A/F ratio sensor control device 30 having the configuration according to the first embodiment does not need to incorporate such a buffer.

Further, the switching element 44 selects the resistances 41, 42, and 43 for amplification as the input resistance and the feedback resistance for the inverting amplification circuit 38, and the amplification factor of the inverting amplification circuit 38 can be set based on the above selection. It is thereby possible to properly adjust the detection resolution of the A/F ratio and accordingly possible to enhance the detection accuracy in a desired air fuel detection range.

Because the amplification factor for the inverting amplification circuit 38 is changed and set based on the input resistance and the feedback resistance selected by the switching element 44, it is possible to provide the sensor control device with a simple configuration when compared with the related art technique using a plurality of operational amplifiers. This can provide the sensor control device and the sensor control system with a small-sized configuration and the reduced number of terminals with a low manufacturing cost.

As described above, according to the first embodiment of the present invention, it is possible to provide the sensor control device with an enhanced detection accuracy in a desired A/F detection range with a simple configuration.

That is, incorporating the switching element 44 into the signal input line of the operational amplifier 39 enables the inverting amplification circuit 38 to amplify the A/F output voltage with a high accuracy. That is, because the signal input line of the operational amplifier 39 has in general a high impedance, it is possible to neglect the presence of a resistance component of the switching element 44 even if the switching element 44 has a resistance component. It is therefore possible to increase the accuracy of the signal amplification by the inverting amplification circuit 38.

Still further, according to the present invention, it is possible to perform the stoichiometry combustion control (or the stoichiometry feedback control) with a high accuracy based on the A/F ratio detection result obtained in the stoichiometry zoom range RG2 and further to perform the lean combustion control (or the lean feedback control) with a high accuracy based on the air-fuel detection result in the lean zoom range RG3. Moreover, it is possible to perform the A/F sensor deterioration diagnosis using the atmosphere detection when the fuel supply to the engine is cut and to perform the rich feedback control when the engine has a high load and a large amount of fuel is supplied to the engine. Furthermore, it is possible to perform the direct injection lean fuel control in which the combustion control is carried out in a super lean region.

Because each A/F ratio detection range described above is set to a detection range including the stoichiometry value, it is possible to easily and effectively perform the diagnosis of the characteristic error of the inverting amplification circuit 38.

Although the sensor control device 30 according to the first embodiment shown in FIG. 1 takes the configuration in which the current detection resistance 32 and the inverting amplification circuit 38 are connected to the positive (+) terminal side of the sensor element 10, the present invention is not limited. For example, it is possible to take a configuration in which the current detection resistance 32 and the inverting amplification circuit 38 are connected to the negative (−) terminal of the sensor element 10.

Second Embodiment

A description will be given of the configuration of the sensor control device 30 according to the second embodiment of the present invention. In the second embodiment, a rich zoom range RG4 as a predetermined fuel-rich control zone is set as the A/F ratio detection range.

Figure 8:
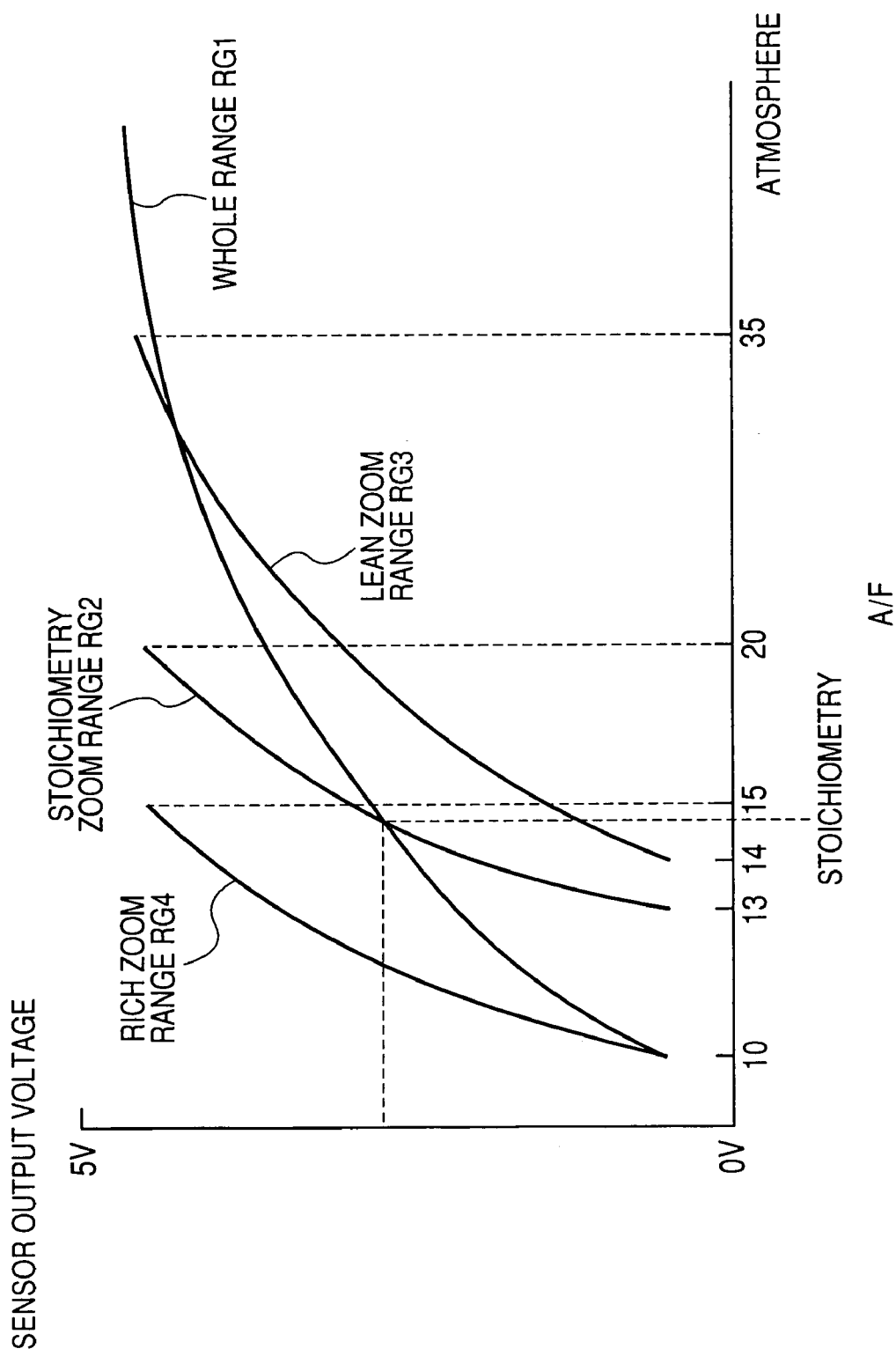
FIG. 8 shows a relationship between the A/F ratio and the output voltage of the sensor element.

FIG. 8 is a view showing a relationship between the A/F ratio and the sensor output voltage. The rich zoom range RG4 is set within the range of A/F=10 to 15, for example. That is, as shown in FIG. 8, the sensor control device according to the second embodiment has the rich zoom range RG4 in addition to the three ranges such as the whole range RG1, the stoichiometry zoom range RG2, and the lean zoom range RG3, described above. Each of those ranges RG1 to RG4 is switched according to the A/F control to be processed.

Figure 9:
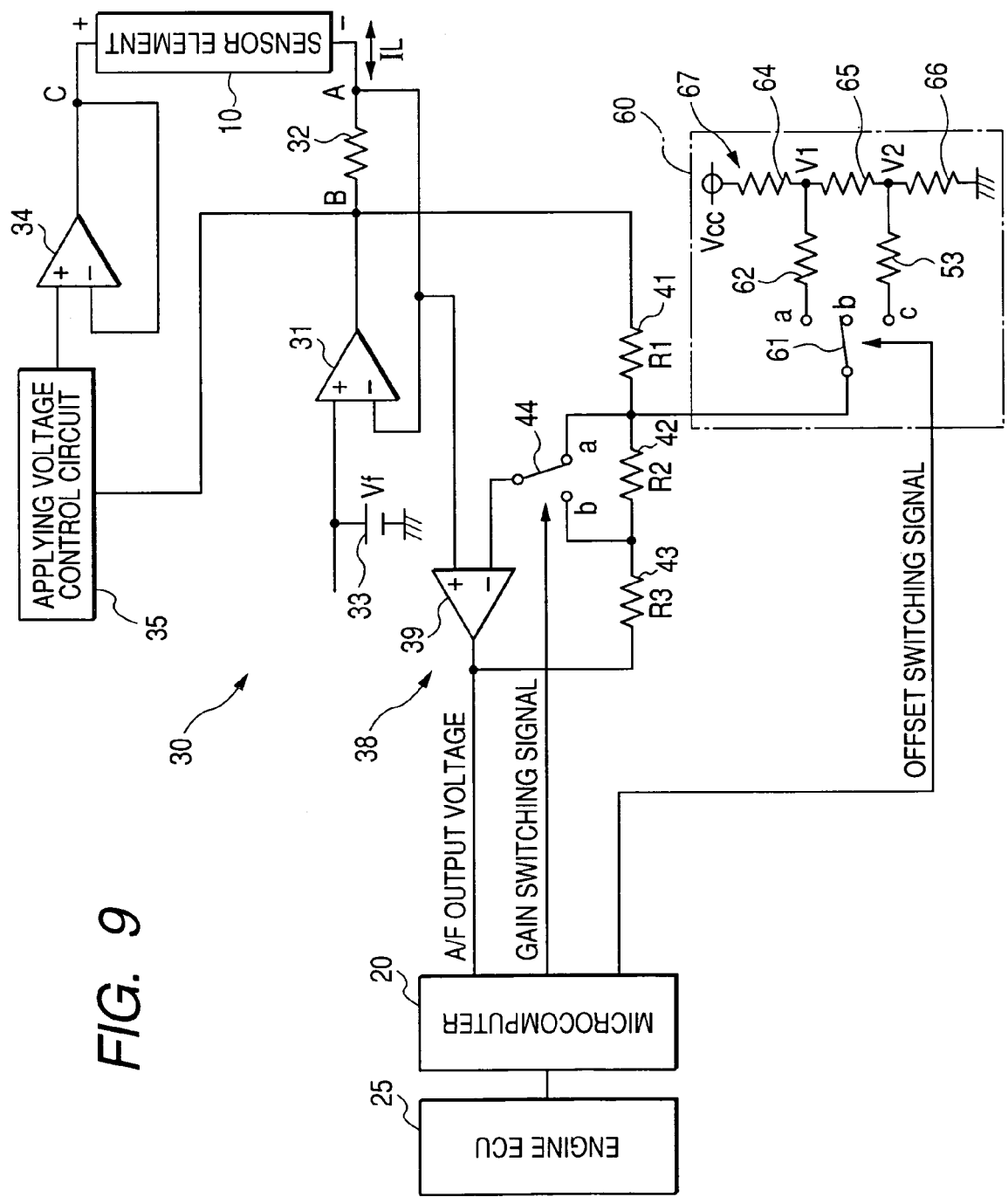
FIG. 9 shows a circuit configuration of a sensor control system equipped with a sensor control device according to a second embodiment of the present invention.

FIG. 9 shows the electrical configuration of the sensor control device 30 in the sensor control system capable of switching the four A/F ratio detection ranges RG1 to RG4 according to the second embodiment of the present invention. The circuit configuration shown in FIG. 9 incorporates an offset setting circuit 60 of a different configuration instead of the offset setting circuit 50 shown in FIG. 1.

Similar to the circuit configuration of the offset setting circuit 50 shown in FIG. 1, the offset setting circuit 60 is disposed at an intermediate node of the resistances 41 and 42 for amplification shown in FIG. 9. The offset setting circuit 60 has a switching element 61 made of a MOS transistor, for example. The switching element 61 has three switching contacts a, b, and c. The switching contacts b and c of the switching element 61 are connected in series to resistances 62 and 63, respectively. Those resistances 62 and 63 are connected to a power source circuit 67 having dividing voltage resistances 64, 65, and 66. Concretely, the resistance 62 is connected to an intermediate node between the dividing voltage resistances 64 and 65. The resistance 63 is connected to an intermediate node between the dividing voltage resistances 65 and 66. The switching element 61 is turned on and off based on the offset switching signal transferred from the microcomputer 20.

The offset switching signal is a control signal to select one of the contacts a, b, and c in order to connect the conductive contact of the switching element 61 to the selected one.

When the offset switching signal indicates that the conductive contact of the switching element 61 is connected to the contact b, the inverting amplification circuit 38 is electrically disconnected from the offset setting circuit 60. In this case, the inverting amplification circuit 38 operates regardless of the output of the offset setting circuit 60. That is, no offset is added to the A/F ratio output voltage.

On the contrary, when the offset switching signal from the microcomputer 20 indicates that the conductive contact of the switching element 61 is connected to one of the contacts a and c, the offset setting to the A/F output voltage from the amplifier 39 is carried out using the power source circuit 67 in the offset setting circuit 60. In this case, one of two offset values is selected by the switching element 61 which selects one of the contacts a and c according to the offset switching signal transferred from the microcomputer 20.

When the conductive contact of the switching element 61 is connected to the contact a, the voltage V1 which is set by the power source circuit 67 is supplied to the inverting amplification circuit 38 through the switching element 61 and others. On the other hand, when the conductive contact of the switching element 61 is connected to the contact c, the voltage V2 which is set by the power source circuit 67 is supplied to the inverting amplification circuit 38 through the switching element 61 and others.

The voltages V1 and V2 to be supplied have the relationship of V1>V2. The voltages V1 and V2 give the inverting amplification circuit 38 a positive offset and a negative offset, respectively. That is, the voltage V1 is a voltage capable of providing a positive current (flowing forward to the operational amplifier 39) corresponding to the offset value supplied to the inverting amplification circuit 38 by the offset setting circuit 60. The voltage V2 is a voltage capable of providing a negative current (flowing backward to the operational amplifier 39) corresponding to the offset value supplied to the inverting amplification circuit 38 by the offset setting circuit 60. Specifically, when it is predicted that both the ends of the current detection resistance 32 have a voltage of 2.2 Volts, V1 becomes approximately 4 Volts, and V2 becomes approximately 1 Volt.

Considering the A/F ratio detection ranges described above, when the A/F ratio detection is carried out in the stoichiometry zoom range RG2, the conductive contact of the switching element 61 is connected to the contact b, and the A/F ratio detection range around the stoichiometry value is realized, as shown in FIG. 8. On the other hand, when the A/F ratio detection is carried out in the lean zoom range RG3, the conductive contact of the switching element 61 is connected to the contact a, and the A/F ratio detection range in a predetermined lean area is realized, as shown in FIG. 8. Still further, when the A/F ratio detection is carried out in the rich zoom range RG4, the conductive contact of the switching element 61 is connected to the contact c, and the A/F ratio detection range in a predetermined rich area is realized, as shown in FIG. 8.

According to the second embodiment described above in detail, it is possible to increase the A/F ratio detection accuracy can be increased. Therefore it is possible to efficiently perform the rich combustion control in addition to the stoichiometry combustion control and the lean combustion control. For example, it is possible to improve or increase the accuracy in performing the rich combustion control under the state of increasing the amount of fuel during a heavy or high load and of the accuracy of carrying out the rich combustion control for regenerating an exhaust gas purifying system (using lean NOx catalyst).

Other Embodiments

The scope of the sensor control device according to the present invention is not limited by the contents of the embodiments described above. For example, the concept of the present invention is applicable to the following cases.

Figure 10A:
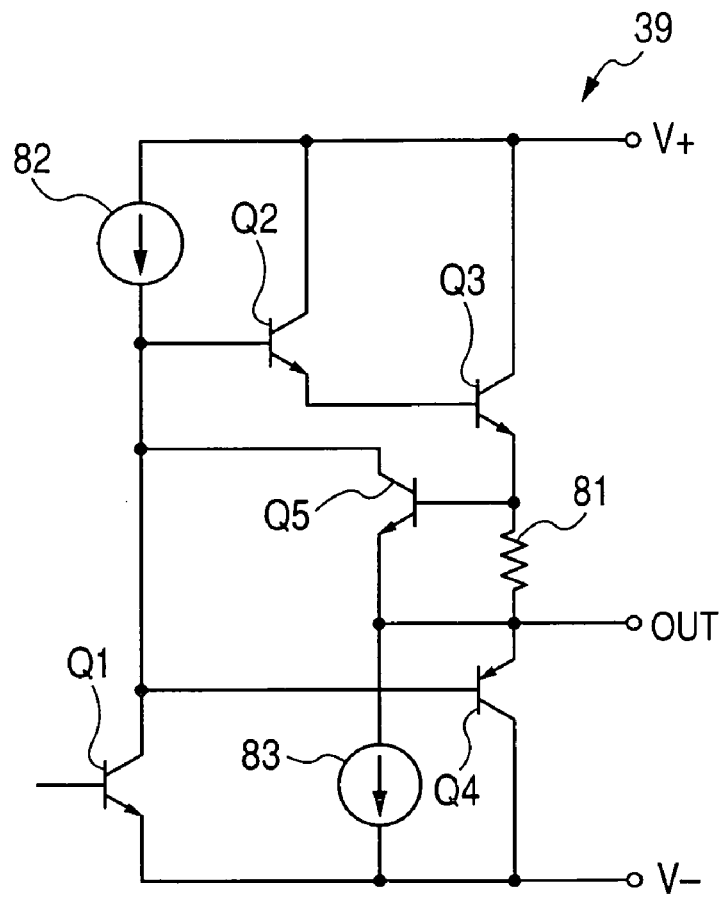
FIG. 10A shows an equivalent circuit diagram of the operational amplifier having another configuration which forms a inverting amplification circuit in the sensor control device according to the second embodiment of the present invention.

FIG. 10A is an equivalent circuit diagram showing the operational amplifier 39 which forms the inverting amplification circuit 38 in the sensor control device 30 (see FIG. 1 or FIG. 9).

In the equivalent circuit shown in FIG. 10A, a collector of an input transistor Q1 is connected to a base of a transistor Q2. An emitter of the transistor Q2 is connected to a base of an output transistor Q3. The collector of the input transistor Q1 is connected to a base of an output transistor Q4. A resistance 81 is connected between the output transistors Q3 and Q4. One end terminal (at the transistor Q3 side) of the resistance 81 is connected to a base of a transistor Q5. The other end terminal (at the transistor Q4 side) of the resistance 81 is connected to an output terminal of the operational amplifier 39. A constant current circuit 83 is connected to a node between an emitter of the transistor Q5 and a ground or earth level line. According to the operational amplifier 39 having the configuration shown in FIG. 10A, the connection between the output terminal and the constant current circuit 83 generates a current flowing into the constant current circuit 83 (a current sink) from the output terminal of the operational amplifier 39. This enables the operational amplifier 39 to output the voltage near the lower limit value of a power-source voltage. That is, it is possible to expand the range of the output voltage of the operational amplifier 39 until the lower limit value of the power source voltage.

Figure 10B:
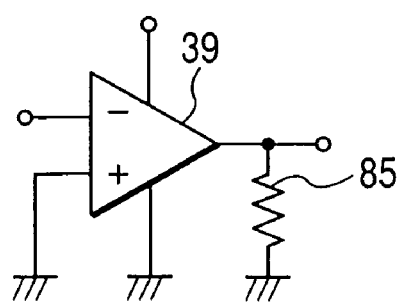
FIG. 10B shows another circuit diagram in which a pull-down resistance is connected to the output terminal of the operational amplifier shown in FIG. 10A.

FIG. 10B shows another circuit configuration in which a pull-down resistance 85 is connected to the output terminal of the operational amplifier 39 shown in FIG. 10A. The circuit configuration as shown in FIG. 10A enables the current to flow from the output terminal of the operational amplifier 39 to the ground through the pull-down resistance 85. Like the circuit configuration as shown in FIG. 10A, it is possible to output the voltage near the lower limit in the electric power voltage.

Using the circuit configurations shown in FIG. 10A and FIG. 10B can provide the sensor control device of a small size, and as a result, provide the small sized chip area with a low price on which the sensor control device is formed.

Although Japanese patent laid open publication No. JP 2006-275628 as one of the related art techniques has disclosed the use of a rail-to-rail operational amplifier capable of obtaining its input/output amplitude near the power source voltage, the operational amplifier having such a circuit configuration is expensive and needs to have a large sized chip area.

Although the sensor control device 30 according to the embodiment described above uses the inverting amplification circuit 38, it is possible to use a non-inverting amplification circuit instead.

Further, although the lean zoom range RG3 is set as the A/F ratio detection range including the stoichiometry value, it is possible to set it as the A/F ratio detection range without including the stoichiometry value. For example, the lean zoom range RG3 is set within a range of A/F=20 to 35. It is also possible to set the rich zoom range RG4 as the A/F ratio detection range without including the stoichiometry value.

Although the sensor control system according to the embodiments described above uses the sensor element (A/F sensor) having the configuration shown in FIG. 2, it is possible to use the sensor element of another element configuration. For example, instead of the sensor element having a single cell, it is possible to use the sensor element having a pump cell and an electromotive force cell. In other words, it is possible to use a double-layer solid polymer electrolyte or a three-layer solid polymer electrolyte (SPE). Still further, it is possible to apply the sensor control device 30 according to the present invention to a cup shaped sensor element instead of the lamination type sensor element.

Third Embodiment

Figure 11A:
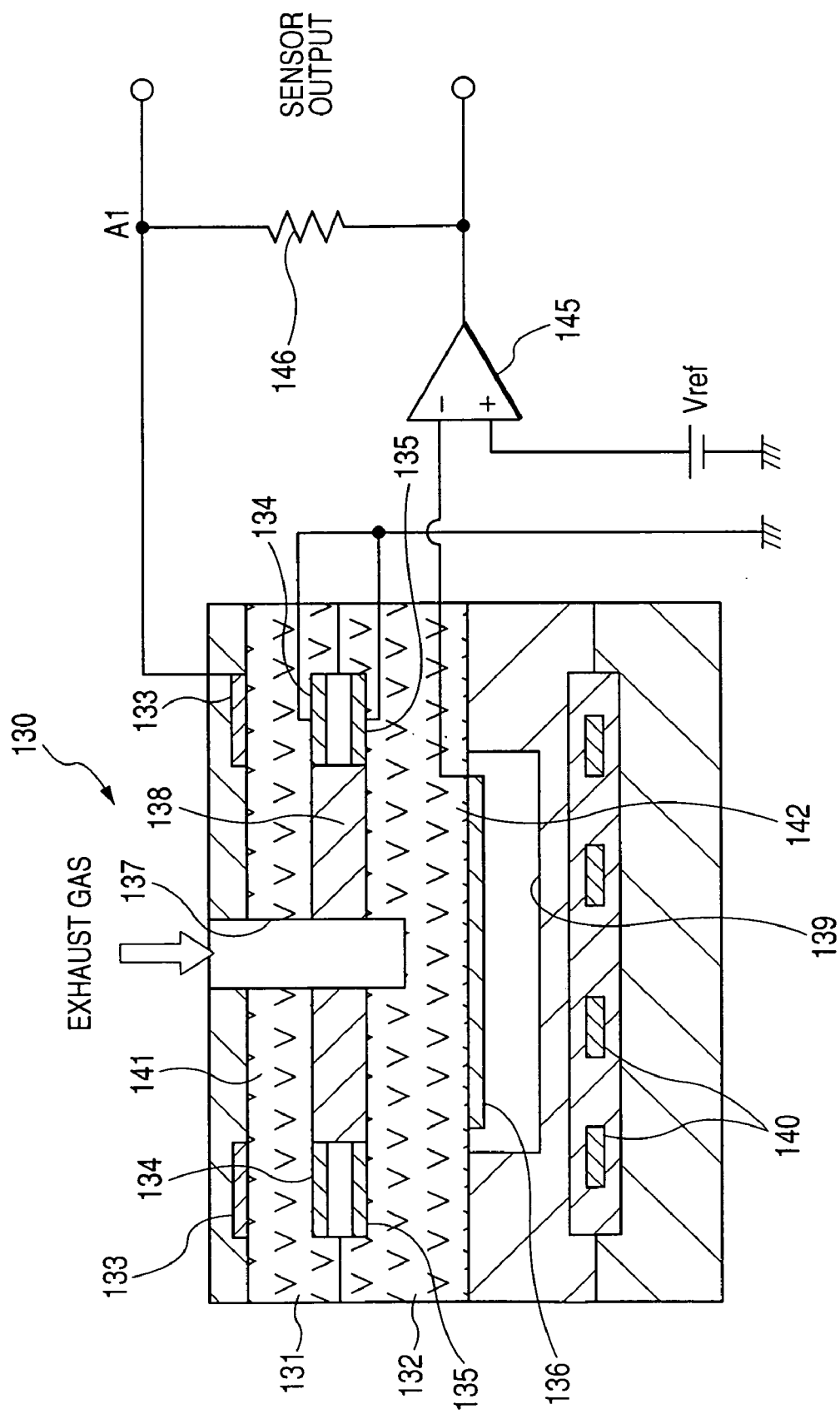
FIG. 11A is a sectional view showing an A/F sensor element having a double cell configuration for use in the sensor control device according to the third embodiment of the present invention.
Figure 11B:
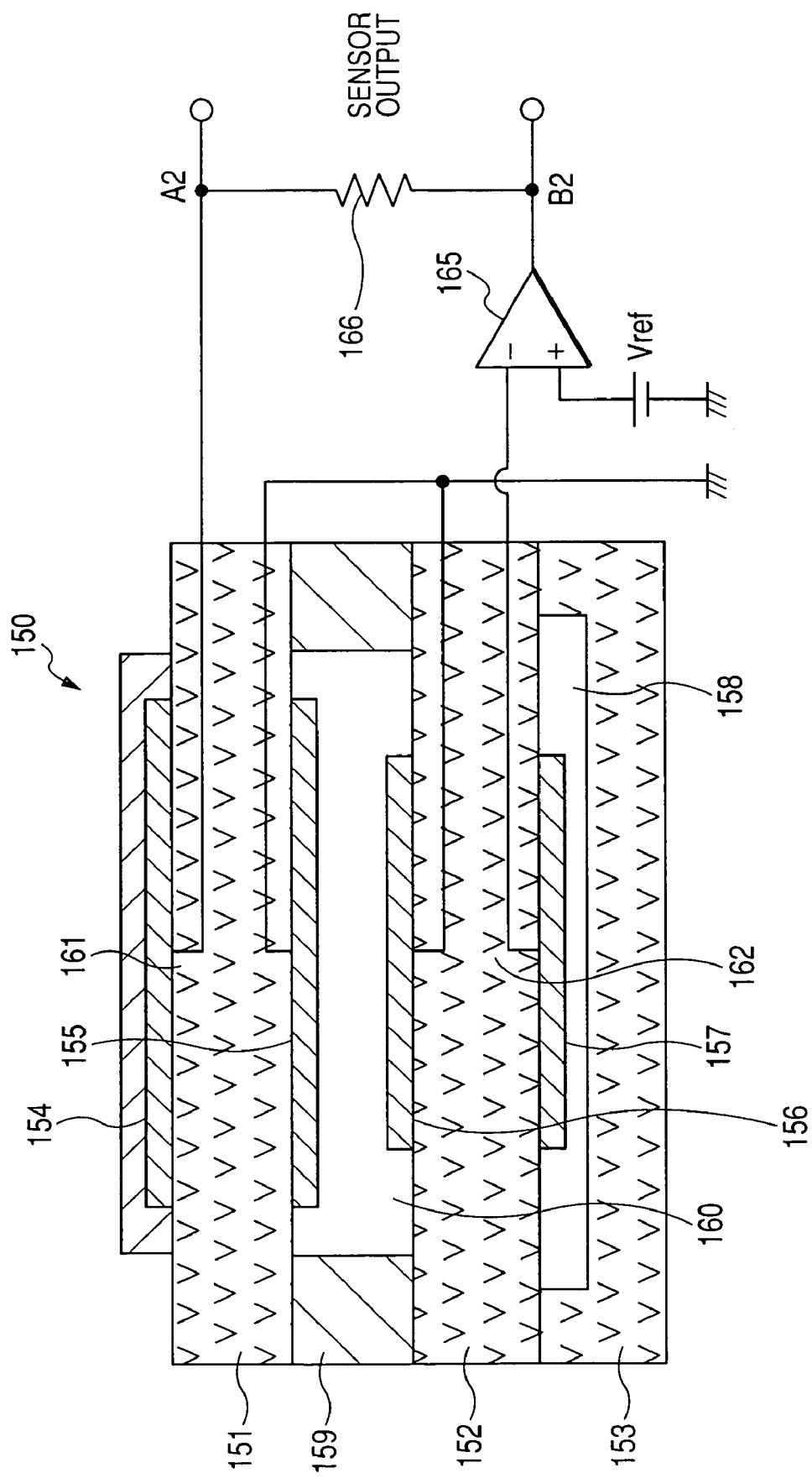
FIG. 11B is a sectional view showing the A/F sensor element having another configuration for use in the sensor control device according to the third embodiment of the present invention.

A description will be given of the configuration of the sensor element and the sensor control device according to the third embodiment of the present invention with reference to FIG. 11A, FIG. 11B, FIG. 12, and FIG. 13. FIG. 11A is a sectional view showing an A/F sensor element having a double cell configuration for use in the sensor control device according to the third embodiment of the present invention. FIG. 11B is a sectional view showing the A/F sensor element having another configuration for us in the sensor control device according to the third embodiment of the present invention.

The sensor element 130, as shown in FIG. 11A, has double solid polymer electrolyte layers 131 and 132. A pair of electrodes 133 and 134 is formed, facing each other, in one solid polymer electrolyte layer 131. On the other hand, a pair of electrodes 135 and 136 is formed, facing each other, in the other solid polymer electrolyte layer 132.

Although FIG. 11A shows the electrodes 133 to 135 in bilateral symmetry, each of them is a single member. In the sensor element 130, the solid polymer electrolyte layer 131 and the electrodes 133 and 134 form a pump cell, and the solid polymer electrolyte layer 132 and the electrodes 135 and 136 form an oxygen detection cell 142. Like the sensor element 10 shown in FIG. 2, the sensor element 130 has a lamination structure or a multi layer structure. In FIG. 11A, reference number 137 designates a gas intake hole, 138 denotes a porous diffusion layer, 139 indicates an ambient atmosphere duct, and 140 designates a heater.

The electrode 136 of the oxygen detection cell 142 in the sensor element 130 is connected to a negative (−) input terminal of a comparator 145. A comparison voltage Vref is supplied to a positive (+) input terminal of the comparator 145. Both ends of a current detection resistance 146 are connected to nodes A1 and B1 between the electrode 133 of the pump cell 141 and the output terminal of the comparator 145. A voltage difference between both the nodes A1 and B1 (corresponding to both the ends) of the resistance 146 is detected as a sensor output voltage of the sensor element 130. The oxygen detection cell 142 in the sensor element 130 having the above configuration generates two voltages (0 Volt and 0.9 Volts) according to the fuel condition such as a fuel lean condition or a fuel rich condition. For example, in the fuel lean condition, the oxygen detection cell 142 generates and outputs a low voltage. On receiving the low voltage from the oxygen detection cell 142, the comparator 145 outputs a high voltage. As a result, the voltage potential at the node B1 rises. At this time, the current flows from the node B1 to the node A1 through the current detection resistance 146.

On the contrary, in the fuel rich condition, the oxygen detection cell 142 generates and outputs a high voltage. On receiving the high voltage from the oxygen detection cell 142, the comparator 145 outputs a low voltage. As a result, the voltage potential at the node B1 is decreased. At this time, the current flows from the node A1 to the node B1 through the current detection resistance 146. The oxygen detection cell 145 is usually called to as an electromotive force cell or an oxygen concentration detection cell.

As shown in FIG. 11B, the sensor element 150 has the three solid polymer electrolyte layers 151, 152, and 153. In the solid polymer electrolyte layer 151, a pair of the electrodes 154 and 155 is formed, facing each other. In the solid polymer electrolyte layer 152, a pair of the electrodes 156 and 157 is formed, facing each other.

In the sensor element 150 shown in FIG. 11B, the solid polymer electrolyte layer 151 and the electrodes 154 and 155 form a pump cell 161, and the solid polymer electrolyte layer 152 and the electrodes 156 and 157 form an oxygen detection cell 162.

The solid polymer electrolyte layer 153 is a wall member which makes an oxygen reference room 158 which accommodates reference oxygen.

Similar to the configuration of the sensor element 10 shown in FIG. 2, the sensor element 150 has a lamination structure or a multi-layer structure.

In FIG. 10B, reference number 159 designates a porous diffusion layer and 160 denotes a gas detection room.

Like the oxygen detection cell 142 shown in FIG. 11A, the oxygen detection cell 162 is usually called to as an electromotive force cell or an oxygen concentration detection cell.

The voltage of the electrode 157 in the oxygen detection cell 162 is input to a negative (−) input terminal of a comparator 165, and the comparison reference voltage Vref is input to a positive (+) input terminal of the comparator 165.

A current detection resistance 166 is connected between the electrode 154 of the pump cell 161 and the output terminal of the comparator 165.

A voltage difference between both the ends A2 and B2 (hereinafter, referred to as the "node A2" and the "node B2") of the resistance 166 is detected as a sensor output voltage of the sensor element 150. The current flows from the node B2 to the node A2 through the current detection resistance 166 during the fuel lean condition in the configuration shown in FIG. 11B. On the contrary, the current flows from the node A2 to the node B2 through the current detection resistance 166 during the fuel rich condition.

A description will now be given of the sensor control system for the sensor element having the double cell configuration.

Figure 12:
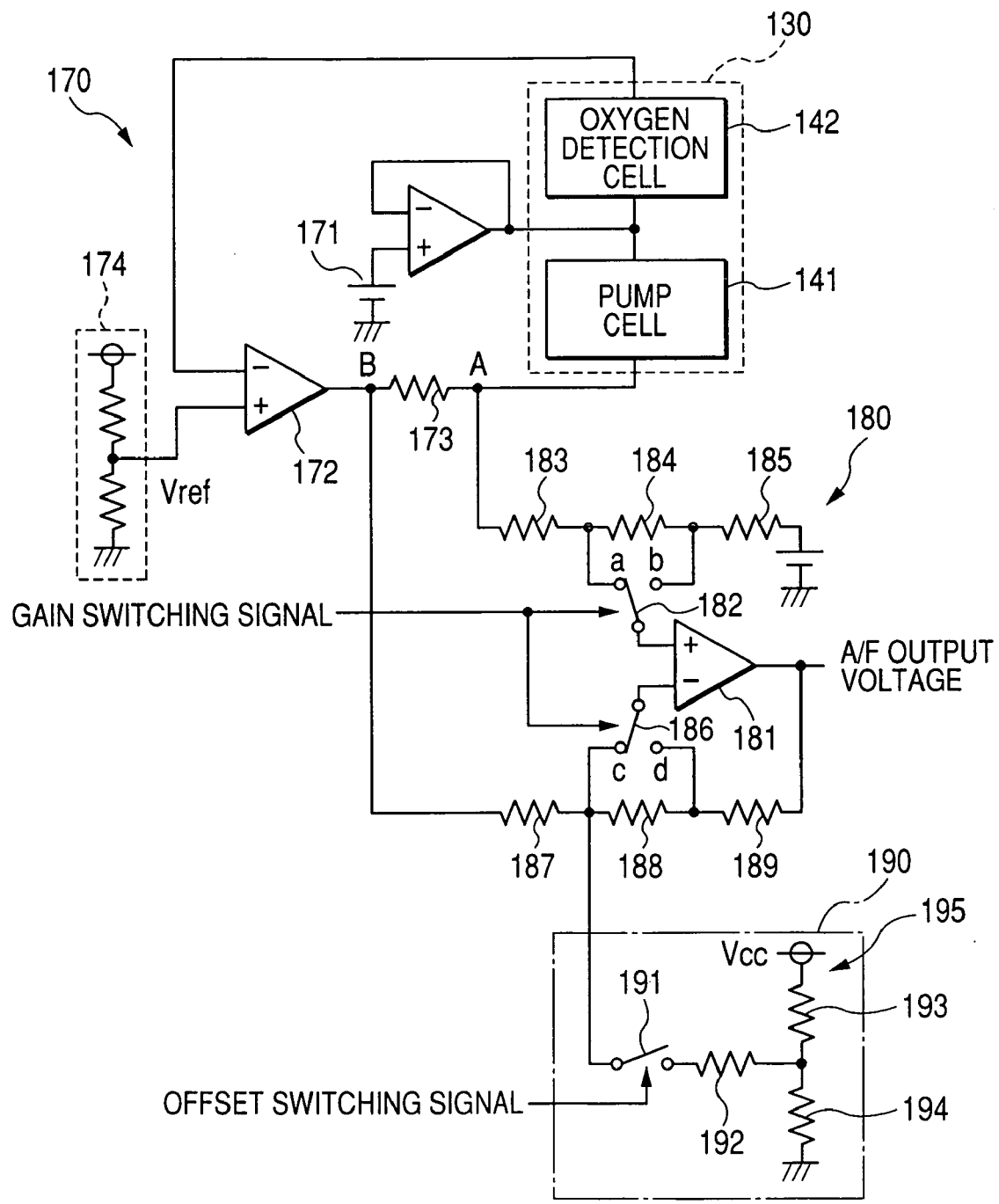
FIG. 12 shows a configuration of the sensor control device for the sensor element shown in FIG. 11A according to the third embodiment of the present invention.

FIG. 12 shows a configuration of the sensor control device 170 for the sensor element 130 shown in FIG. 11A.

In the sensor control device 170 shown in FIG. 12, a common terminal of the pump cell 141 and the oxygen detection cell 142 in the sensor element 130 is connected to a reference voltage power source 171. The pump cell 141 and the oxygen detection cell 142, an operational amplifier 172 and a current detection resistance 173 form a closed circuit. A non-inverting input terminal (positive (+) input terminal) of the operational amplifier 172 is connected to a comparison voltage generation circuit 174 for generating a comparison reference voltage Vref (=0.45 Volts). In the fuel lean condition, the current flows from the node B3 to the node A3 through a current detection resistance 173. On the contrary, in the fuel rich condition, the current flows from the node A3 to the node B3 through the current detection resistance 173.

The operational amplifier 172 shown in FIG. 12 corresponds to the operational amplifier 145 shown in FIG. 11A, and the current detection resistance 173 shown in FIG. 12 corresponds to the current detection resistance 146 shown in FIG. 11A. In this case, the feedback control for the pump cell 141 is performed so that the output voltage at the oxygen detection cell 142 becomes a predetermined voltage.

Because the configuration and control of the feedback control circuit have been disclosed in well-known related-art documents, the explanation for them is omitted here.

The differential amplifier 180 is connected between both the ends A3 and B3 of the current detection resistance 173. The differential amplifier 180 inputs the voltages at the node A3 and the node B3 of the current detection resistance 173 and amplifies the voltage difference between those nodes A3 and B3. The differential amplifier 180 then outputs an A/F output voltage to the microcomputer 20 (omitted from FIG. 12).

The differential amplifier 180 has an operational amplifier 181. A switching element 182 is placed at an input line connected to the positive (+) input terminal of the operational amplifier 181. Switching contacts a and b for the switching element 182 are connected to both ends of an amplification resistance 184, respectively.

The amplification resistance 184 is disposed between the amplification resistances 183 and 185. That is, the resistances 183, 184, and 185 for amplification are connected in series. The switching element 182 is conducted to one of the switching contacts a and b.

A switching element 186 is disposed on a signal input line connected to a negative (−) input terminal (as an inverting input terminal) of the operational amplifier 181. Switching contacts c and d for the switching element 186 are connected to both ends of an amplification resistance 188, respectively. The amplification resistance 188 is disposed between the resistances 187 and 189 for amplification. That is, the resistances 187, 188, and 189 for amplification are connected in series. In this case, the switching element 186 is conducted to both the negative (−) input terminal of the operational amplifier 181 and the switching contact c, as shown in FIG. 12.

When receiving a gain switching signal transferred from the microcomputer 20 (not shown), both the switching elements 182 and 186 perform the switching operation simultaneously. According to the switching operation by the switch elements 182 and 186, the amplification factor of the differential amplifier 180 is changed.

Because the relationship between the amplification factor and the A/F ratio detection range has been described above, the explanation of this is omitted here.

The differential amplifier 180 keeps following states before and after the switching operation by the switching elements 182 and 186.

A positive input resistance value is equal to a negative input resistance value; and A feedback resistance value is equal to an input resistance value.

In a feedback line for the differential amplifier 180, an offset setting circuit 190 is connected to an intermediate node between (or a common node of) the amplification resistances 187 and 188. The offset setting circuit 190 gives the offset to the A/F output voltage from the differential amplifier 180. Giving the offset to the A/F output voltage from the differential amplifier 180 can change the A/F ratio detection range.

The differential amplifier 180 and the offset setting circuit 190 form an adder circuit. The differential amplifier 180 outputs the A/F output voltage as the voltage signal which is obtained by adding the element current signal, which corresponds to the magnitude of the element current IL, to the offset signal.

The offset setting circuit 190 comprises a switching element 191 composed of a MOS transistor, a resistance 192 connected to the switching element 191 in series, a power source circuit 195 having two dividing voltage resistances 193 and 194.

The switching element 191 is turned on and off based on the offset switching signal transferred from the microcomputer 20 (not shown).

When receiving the offset switching signal of a low level, the switching element 191 is turned off. Specifically, the differential amplifier 180 is disconnected from the offset setting circuit 190, the differential amplifier 180 operates regardless of the output of the offset setting circuit 190. That is, any offset setting operation for the A/F output voltage is not performed.

On the contrary, when receiving the offset switching signal of a high level, the switching element 191 is turned on. The differential amplifier 180 operates using the offset by the offset setting circuit 190 under the condition where the differential amplifier 180 is connected to the offset setting circuit 190. That is, the offset current flows, which is determined by the resistance 192 and the power source circuit 195 into the offset setting circuit 190, into the differential amplifier 180 (namely, into the operational amplifier 181), and the offset value is given to the A/F output voltage of the differential amplifier 180 based on the magnitude of the offset current from the offset setting circuit 190.

When the A/F ratio detection is performed in the stoichiometry zoom range RG2, the switching element 191 is turned off in order to select the A/F ratio detection range around the stoichiometry value, like the whole range RG1. When the A/F ratio detection is performed in the lean zoom range RG3, the switching element 191 is turned off, so that the A/F ratio detection is performed in a predetermined lean range.

In the configuration of the sensor control device 200 shown in FIG. 12, it is switched according to the offset switching operation that the middle node between the input resistance in the feedback line in the differential amplification circuit 180 and the feedback resistances is connected or not connected to the offset setting circuit 190. In this case, before and after the switching operation, it is maintained that the value of the feedback resistance of the differential amplifier 180 is equal to the value of the ground resistance. Accordingly, it is possible to avoid the occurrence of fluctuating the signal amplification factor and the gas concentration detection range, contrary to the expectation, along with the offset switching operation, and possible to realize the optimum A/F ratio detection operation.

In the sensor control device 170 shown in FIG. 12, the voltage potential at the node A3 and the voltage potential at the node B3 of the current detection resistance 173 are varied, not fixed. On the contrary, in the sensor control device 200 shown in FIG. 13, the voltage potential at one end of the current detection resistance 202 is fixed.

Figure 13:
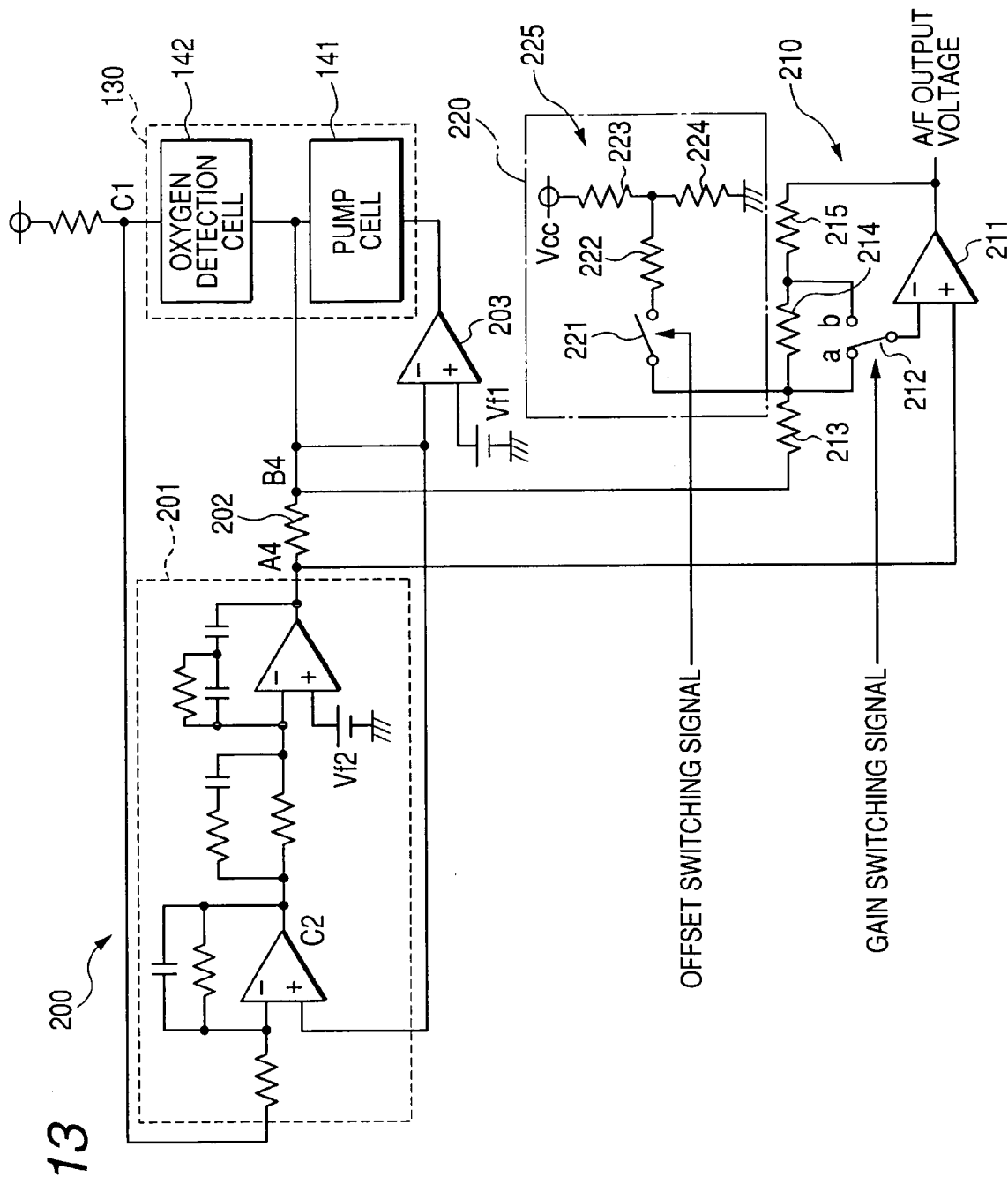
FIG. 13 shows another configuration of the sensor control device for the sensor element shown in FIG. 11A according to the third embodiment of the present invention.

FIG. 13 shows another configuration of the sensor control device 200 for the sensor element 130 according to the third embodiment of the present invention. As shown in FIG. 13, the voltage (for example, 3 Volts) which is equal to the reference voltage Vf1 is supplied to a common terminal of the pump cell 141 and the oxygen detection cell 142 in the sensor element 200 through the operational amplifier 203. That is, the voltage potential at the node B4 of the resistance 202 is fixed to 3 Volts. In FIG. 13, a closed circuit composed of a feedback circuit 201 and a current detection resistance 202 is made. The reference voltage Vf2 in the feedback circuit 201 is 2.55 Volts, for example.

A description will now be given of the operation of the sensor control device 200 during the fuel rich condition shown in FIG. 13.

In the fuel rich condition, because the voltage potential at the node C1 rises to 3.45 Volts by the electromotive force of the oxygen detection cell 142, the voltage potential at the node C2 in the feedback circuit 201 is decreased. At this time, the output voltage of the feedback circuit 201, namely, the voltage potential at the node A4 is increased. In the fuel rich condition, the current flows from the node A4 to the node B4 in the current detection resistance 202. On the contrary, the current flows from the node B4 to the node A4 in the current detection resistance 202 during the fuel lean condition.

An inverting type amplification circuit 210 is connected to both the nodes A4 and B4 of the current detection resistance 202. The A/F output voltage output from the inverting type amplification circuit 210 is output to the microcomputer (not shown). The inverting type amplification circuit 210 has an operational amplifier 211. In the inverting type amplification circuit 210, a switching element 212 is disposed on a signal input line connected to the negative (−) input terminal (inverting input terminal) of the operational amplifier 211. Further, the switching contacts a and b of the switching element 212 are connected to the both ends of the resistance 214 for amplification. The resistance 214 is disposed between the resistances 213 and the resistance 215. Those resistances 213 to 215 are used for amplification. In this case, the negative (−) input terminal of the operational amplifier 211 is connected to the contact a by the switching element 212.

When receiving a gain switching signal transferred from the microcomputer 20 (not shown), the switching element 212 performs the switching operation. In this case, the amplification factor of the amplification circuit 210 is changed according to the switching operation of the switching element 212. Because the relationship between the amplification factor and the A/F ratio detection range has been described above, the explanation of this is omitted here.

In FIG. 13, the offset setting circuit 210 is connected to the middle node between the resistances 213 and 214 for amplification in the feedback line of the inverting type amplification circuit 210. The offset setting circuit 220 gives the offset to the A/F output voltage supplied from the amplification circuit 210. Giving the offset to the A/F output voltage from the amplification circuit 210 can change the A/F ratio detection range.

The amplification circuit 210 and the offset setting circuit 220 form an adder circuit. The amplification circuit 210 outputs the A/F output voltage as the voltage signal which is obtained by adding the element current signal, which corresponds to the magnitude of the element current IL, to the offset signal.

The offset setting circuit 220 comprises a switching element 221 composed of a MOS transistor, a resistance 222 connected to the switching element 221 in series, a power source circuit 225 having two dividing voltage resistances 223 and 224. The switching element 221 is turned on and off based on the offset switching signal transferred from the microcomputer (not shown).

When receiving the offset switching signal of a low level, the switching element 221 is turned off. Specifically, the amplification circuit 210 is disconnected from the offset setting circuit 220, the amplification circuit 210 operates regardless of the output of the offset setting circuit 220. That is, any offset setting for the A/F output voltage is not performed.

On the contrary, when receiving the offset switching signal of a high level, the switching element 221 is turned on. The amplification circuit 210 operates using the offset which is determined by the offset setting circuit 220 under the condition in which the amplification circuit 210 is connected to the offset setting circuit 220. That is, the offset current flows, which is determined by the resistance 222 and the power source circuit 225 in the offset setting circuit 220, into the amplification circuit 210 (namely, into the operational amplifier 211), and the offset is given to the A/F output voltage of the amplification circuit 210 based on the magnitude of the offset current from the offset setting circuit 220.

When the A/F ratio detection is performed in the stoichiometry zoom range RG2, the switching element 221 is turned off in order to select the A/F ratio detection range around the stoichiometry value, like the whole range RG1. When the A/F ratio detection is performed in the lean zoom range RG3, the switching element 221 is turned off, so that the A/F ratio detection is performed in a predetermined lean range.

Like the circuit configuration of the sensor control device shown in FIG. 12, in the configuration of the sensor control device 200 shown in FIG. 13, the connection state and the disconnection state between the offset setting circuit 220 and the middle node between the input resistance and the feedback resistances in the feedback line of the differential amplification circuit 210 are switched according to the offset switching signal. Accordingly, it is possible to avoid the occurrence of fluctuating the signal amplification factor and the gas concentration detection range, contrary to the expectation, along with the offset switching operation, and possible to realize the optimum a/f ratio detection operation.

The sensor control device according to the present invention is applicable to gas concentration sensors capable of detecting another gas concentration other than the A/F sensor which detects the oxygen concentration. For example, a complex type gas concentration sensor has a plurality of cells made of solid polymer electrolyte in which a primary cell (or a pump cell) discharges or pumps out oxygen in a target detection gas to be detected, a secondary cell (or a sensor cell) detects a gas concentration of a specified component in the gas after oxygen is discharged from the target detection gas. Such a gas concentration sensor is used as a NOx sensor capable of detecting the concentration of NOx component contained in exhaust gas, for example. Applying the sensor control device according to the present invention to such a gas concentration sensor can improve the detection accuracy of the NOx concentration. The complex type gas concentration sensor has a third cell (a monitor cell or a secondary pump cell) in addition to the primary and secondary cells which are capable of detecting a concentration of remaining or residual oxygen after discharging oxygen from the exhaust gas.

The sensor control device according to the present invention is applicable to a gas concentration sensor for detecting the concentration of a HC or CO as components in a gas. In this case, the pump cell discharges excess oxygen in a target detection gas, a sensor cell decomposes HC and CO in the gas after discharging excess oxygen and detects the concentration of HC and CO.

Further, the censor control device according to the present invention is applicable to various types of gas sensors (sensor elements) for diesel engines and other type engines in addition to the gas sensor (sensor element) for gasoline engines. It is further possible to use the censor control device according to the present invention as a sensor control device for various applications other than motor vehicles. Still further, the censor control device according to the present invention is applicable to gas sensors capable of detecting various types of gases other than exhaust gas.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalent thereof.

What is claimed is:

1. A sensor control device for controlling the operation of a sensor element made up of solid polymer electrolyte capable of detecting a concentration of a specific gas component contained in a target gas in a wide detection range, comprising:
   a current detection resistance for detecting a current flowing in the sensor element and generating a terminal voltage which corresponds to the detected current;
   an amplification circuit comprised of an operational amplifier, an input resistance and a feedback resistance, the input resistance and the feedback resistance being connected to the operational amplifier, a positive or negative input signal terminal of the operational amplifier inputting an element current signal as the detected terminal voltage at the current detection resistance, and the operational amplifier amplifying the element current signal on the basis of a ratio between the input resistance and the feedback resistance;
   an offset setting circuit for flowing an offset current in a connection node between the input resistance and the feedback resistance in the amplification circuit in order to offset an output signal of the operational amplifier on the basis of the offset current; and
   offset switching device for switching the offset determined by the offset setting circuit on the basis of the element current signal, which is continuously supplied from the sensor element, regarding the concentration of the specific gas component contained in the target gas;
   wherein the amplification circuit comprises a first resistance which is always at least part of the input resistance, and a third resistance which is always at least part of the feedback resistance, and a second resistance which is selected by the offset switching device to become part of either the input resistance or the feedback resistance, the input resistance and the feedback resistance being selected by an amplification factor switching device in order to determine the amplification factors of the amplification circuit.

2. The sensor control device according to claim 1, wherein the offset setting circuit sets a plurality of offset values, and the offset switching device selectively selects one of the plurality of offset values.

3. The sensor control device according to claim 1, wherein the target gas is an exhaust gas emitted from an internal combustion engine, and the sensor control device detects an air/fuel (A/F) ratio of the exhaust gas in an A/F ratio detection range, and
   the A/F ratio detection range comprises:
   a stoichiometry detection range for use in a stoichiometry combustion control, which is as a part of the whole A/F ratio detection range detectable by the sensor element: and
   a lean detection range for use in a lean combustion control, which is as a part of the whole A/F ratio detection range detectable by the sensor element, wherein the offset switching device judges whether the A/F ratio detection is performed under the stoichiometry detection range or the lean detection range according to the A/F ratio control, and
the offset switching device switches the offset according to the judgment result.

4. The sensor control device according to claim 3, wherein the A/F ratio detection range includes a rich detection range for use in a rich combustion control as a part of the whole A/F ratio detection range,
the offset switching device selects one of the stoichiometry detection range, the lean detection range, and the rich detection range in order to detect the A/F ratio using the selected one, and switches the offset based on the judgment result.

5. The sensor control device according to claim 3, wherein each of the stoichiometry detection range, the lean detection range, and the rich detection range includes a stoichiometry value.

6. The sensor control device according to claim 5, further comprising a circuit characteristic detector configured to detect a circuit characteristic error based on an output signal of the amplification circuit at the time when the current flowing in the sensor element is forcedly halt.

7. The sensor control device according to claim 1, wherein the wide detection range for detecting the gas concentration of the specific gas component contained in the target gas is divided into different detection ranges in advance,
the amplification factor switching device switches the resistances for amplification so that the amplification factor of the amplification circuit is increased when the gas concentration of the specific gas component contained the target gas is detected in a narrow detection range in the different detection ranges, and switches the resistances for amplification so that the amplification factor of the amplification circuit is decreased when the gas concentration of the specific gas component contained in the target gas is detected in a wide detection range in the different detection ranges.

8. The sensor control device according to claim 1, wherein the target detection gas is an exhaust gas emitted from an internal combustion engine,
the sensor control device detects an A/F ratio of the exhaust gas in an A/F ratio detection range, and
the A/F ratio detection range comprises:
a whole A/F ratio detection range in which the sensor element is detectable;
a stoichiometry detection range, which is a part of the whole A/F ratio detection range, for use in a stoichiometry combustion control; and
a lean detaction range, which is a part of the whole A/F ratio detection range,
for use in a lean combustion control in a part of the whole A/F ratio detection range, the sensor control device so controls that:
the offset switching device does not give any offset to the amplification circuit when the sensor element detects the A/F ratio of the exhaust gas under the whole A/F ratio detection range, and the amplification factor switching device selects the resistances for amplification so that the amplification factor is decreased;
the offset switching device does not give any offset when the sensor element detects the A/F ratio of the exhaust gas under the stoichiometry detection range, and the amplification factor switching device selects the resistances for amplification so that the amplification factor is increased; and
the offset switching device gives an offset when the sensor element detects the A/F ratio of the exhaust gas under the lean detection range, and the amplification factor switching device selects the resistances for amplification so that the amplification factor is increased.

9. The sensor control device according to claim 7, wherein the target detection gas is an exhaust gas emitted from an internal combustion engine,
the sensor control device detects an A/F ratio of the exhaust gas in an A/F ratio detection range, and
the A/F ratio detection range comprises:
a whole A/F ratio detection range in which the sensor element is detectable;
a stoichiometry detection range, which is a part of the whole A/F ratio detection range, for use in a stoichiometry combustion control; and
a lean detaction range, which is a part of the whole A/F ratio detection range,
for use in a lean combustion control in a part of the whole A/F ratio detection range, the sensor control device so controls that:
the offset switching device does not give any offset to the amplification circuit when the sensor element detects the A/F ratio of the exhaust gas under the whole A/F ratio detection range, and the amplification factor switching device selects the resistances for amplification so that the amplification factor is decreased;
the offset switching device does not give any offset when the sensor element detects the A/F ratio of the exhaust gas under the stoichiometry detection range, and the amplification factor switching device selects the resistances for amplification so that the amplification factor is increased; and
the offset switching device gives an offset when the sensor element detects the A/F ratio of the exhaust gas under the lean detection range, and the amplification factor switching device selects the resistances for amplification so that the amplification factor is increased.

10. The sensor control device according to claim 8, wherein the sensor control device detects the A/F ratio of the exhaust gas in the A/F ratio detection range, and the A/F ratio detection range is further comprised of a rich detection range, which is a part of the whole A/F ratio detection range, for use in a rich combustion control, and
the sensor control device so controls that the offset switching device gives an inverted offset, which is obtained by inverting the offset for use in the lean detection range, when the sensor element detects the A/F ratio of the exhaust gas under the rich detection range, and the amplification factor switching device selects the resistances for amplification so that the amplification factor is increased.

11. The sensor control device according to claim 1, wherein the amplification circuit comprises one of a constant current source and a pull-down resistance placed at an output stage thereof.

* * * * *